US011730807B2

United States Patent
Fujisawa et al.

(10) Patent No.: US 11,730,807 B2
(45) Date of Patent: *Aug. 22, 2023

(54) MULTIVALENT RECOMBINANT AVIAN HERPES VIRUSES AND VACCINES FOR IMMUNIZING AVIAN SPECIES

(71) Applicant: CEVA SANTE ANIMALE, Libourne (FR)

(72) Inventors: Ayumi Fujisawa, Kanagawa (JP); Mayumi Kubomura, Kanagawa (JP); Sakiko Saeki, Tokyo (JP); Shuji Saito, Kanagawa (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/475,385

(22) Filed: Sep. 15, 2021

(65) Prior Publication Data

US 2021/0401973 A1    Dec. 30, 2021

Related U.S. Application Data

(63) Continuation of application No. 16/707,106, filed on Dec. 9, 2019, now Pat. No. 11,123,425, which is a continuation of application No. 15/972,283, filed on May 7, 2018, now Pat. No. 10,500,270, which is a continuation of application No. 14/388,268, filed as application No. PCT/EP2013/056839 on Mar. 29, 2013, now Pat. No. 10,251,951.

(30) Foreign Application Priority Data

Mar. 30, 2012    (EP) .................... 12305390

(51) Int. Cl.
| | |
|---|---|
| *A61K 39/245* | (2006.01) |
| *C12N 15/86* | (2006.01) |
| *A61K 39/12* | (2006.01) |
| *A61K 39/17* | (2006.01) |
| *C12N 7/00* | (2006.01) |
| *A61K 39/00* | (2006.01) |

(52) U.S. Cl.
CPC ............ *A61K 39/245* (2013.01); *A61K 39/12* (2013.01); *A61K 39/17* (2013.01); *C12N 7/00* (2013.01); *C12N 15/86* (2013.01); *A61K 2039/5256* (2013.01); *A61K 2039/552* (2013.01); *A61K 2039/70* (2013.01); *C12N 2710/16321* (2013.01); *C12N 2710/16334* (2013.01); *C12N 2710/16343* (2013.01); *C12N 2720/10034* (2013.01); *C12N 2760/18134* (2013.01)

(58) Field of Classification Search
CPC ...... A61K 39/245; A61K 39/12; A61K 39/17; A61K 2039/5256; A61K 2039/552; A61K 2039/70; C12N 7/00; C12N 15/86; C12N 2710/16321; C12N 2710/16334; C12N 2710/16343; C12N 2720/10034; C12N 2760/18134; A61P 31/22; A61P 37/04
See application file for complete search history.

(56) References Cited

U.S. PATENT DOCUMENTS

| | | |
|---|---|---|
| 5,980,906 A | 11/1999 | Audonnet et al. |
| 10,245,315 B2 | 4/2019 | Fujisawa et al. |
| 10,251,951 B2 | 4/2019 | Fujisawa et al. |
| 10,500,270 B2 | 12/2019 | Fujisawa et al. |
| 11,123,425 B2 | 9/2021 | Fujisawa et al. |
| 2011/0223195 A1 | 9/2011 | Gardin et al. |
| 2016/0220657 A1 | 8/2016 | Esaki et al. |
| 2018/0256706 A1 | 9/2018 | Fujisawa et al. |

FOREIGN PATENT DOCUMENTS

| | | |
|---|---|---|
| WO | WO 03/064595 | 8/2003 |
| WO | WO 2010/119112 | 10/2010 |
| WO | WO 2013/057236 | 4/2013 |

OTHER PUBLICATIONS

Tang N, Zhang Y, Sadigh Y, Moffat K, Shen Z, Nair V, Yao Y. Generation of A Triple Insert Live Avian Herpesvirus Vectored Vaccine Using CRISPR/Cas9-Based Gene Editing. Vaccines (Basel). Feb. 21, 2020;8(1):97. (Year: 2020).*
Gowthaman V, Kumar S, Koul M, Dave U, Murthy TRGK, Munuswamy P, Tiwari R, Karthik K, Dhama K, Michalak I, Joshi SK. Infectious laryngotracheitis: Etiology, epidemiology, pathobiology, and advances in diagnosis and control—a comprehensive review. Vet Q. Dec. 2020;40(1):140-161. (Year: 2020).*
Kingsley DH, Keeler CL Jr. Infectious laryngotracheitis virus, an alpha herpesvirus that does not interact with cell surface heparan sulfate. Virology. Apr. 10, 1999;256(2):213-9. (Year: 1999).*
Ji Y, Liu T, Jia Y, Liu B, Yu Q, Cui X, Guo F, Chang H, Zhu Q. Two single mutations in the fusion protein of Newcastle disease virus confer hemagglutinin-neuraminidase independent fusion promotion and attenuate the pathogenicity in chickens. Virology. Sep. 2017;509:146-151. Epub Jun. 21, 2017. (Year: 2017).*
Gergen L, Cook S, Ledesma B, Cress W, Higuchi D, Counts D, Cruz-Coy J, et al. A double recombinant herpes virus of turkeys for the protection of chickens against Newcastle, infectious laryngotracheitis and Marek's diseases. Avian Pathol. Feb. 2019;48(1):45-56. Epub Nov. 30, 2018. (Year: 2018).*

(Continued)

*Primary Examiner* — Rachel B Gill
(74) *Attorney, Agent, or Firm* — Saliwanchik, Lloyd & Eisenschenk

(57) ABSTRACT

The present invention relates to a recombinant *avian* herpes virus, which comprises at least two recombinant nucleotide sequences, each recombinant nucleotide sequence encoding a distinct antigenic peptide, wherein the at least two recombinant nucleotide sequences are inserted into distinct non-coding regions of the viral genome chosen among the region located between UL44 and UL45, the region located between UL45 and UL46, the region located between US10 and SORF3, and the region located between SORF3 and US2.

7 Claims, 8 Drawing Sheets

Specification includes a Sequence Listing.

(56) References Cited

OTHER PUBLICATIONS

Tsukamoto, K. et al. "Complete, Long-Lasting Protection against Lethal Infectious Bursal Disease Virus Challenge by a Single Vaccination with an Avian Herpesvirus Vector Expressing VP2 Antigens" *Journal of Virology*, Jun. 1, 2002, pp. 5637-5645, vol. 76, No. 11.

Reddy, S.K. et al. "Protective efficacy of a recombinant herpesvirus of turkeys as an in ovo vaccine against Newcastle and Marek's diseases in specific-pathogen-free chickens" *Vaccine*, Apr. 1, 1996, pp. 469-477, vol. 14, No. 6.

Krisky, D. M. et al. "Development of herpes simplex virus replication-defective multigene vectors for combination gene therapy applications" *Gene Therapy*, Nov. 1998, pp. 1517-1530, vol. 5, No. 11.

Afonso, C. L. et al. "Meleagrid herpesvirus 1 strain FC126, complete genome" GenBank: AF291866.1, Dep. Jan. 25, 2001, pp. 1-54.

\* cited by examiner

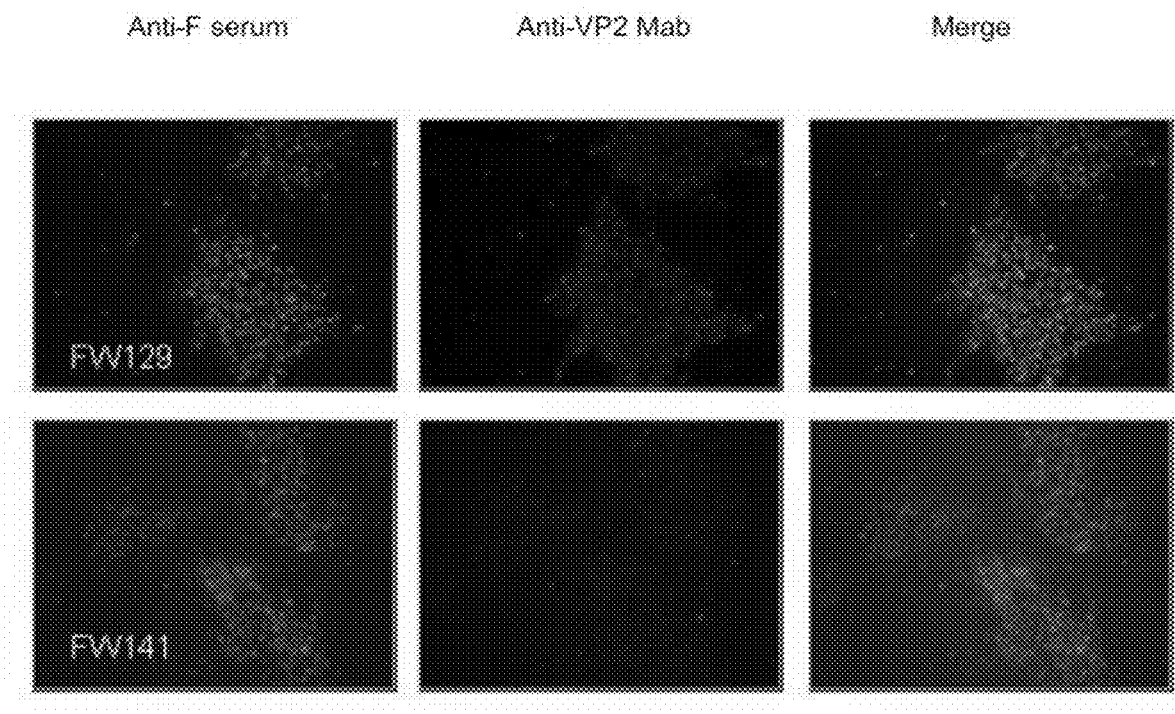
Fig. 3
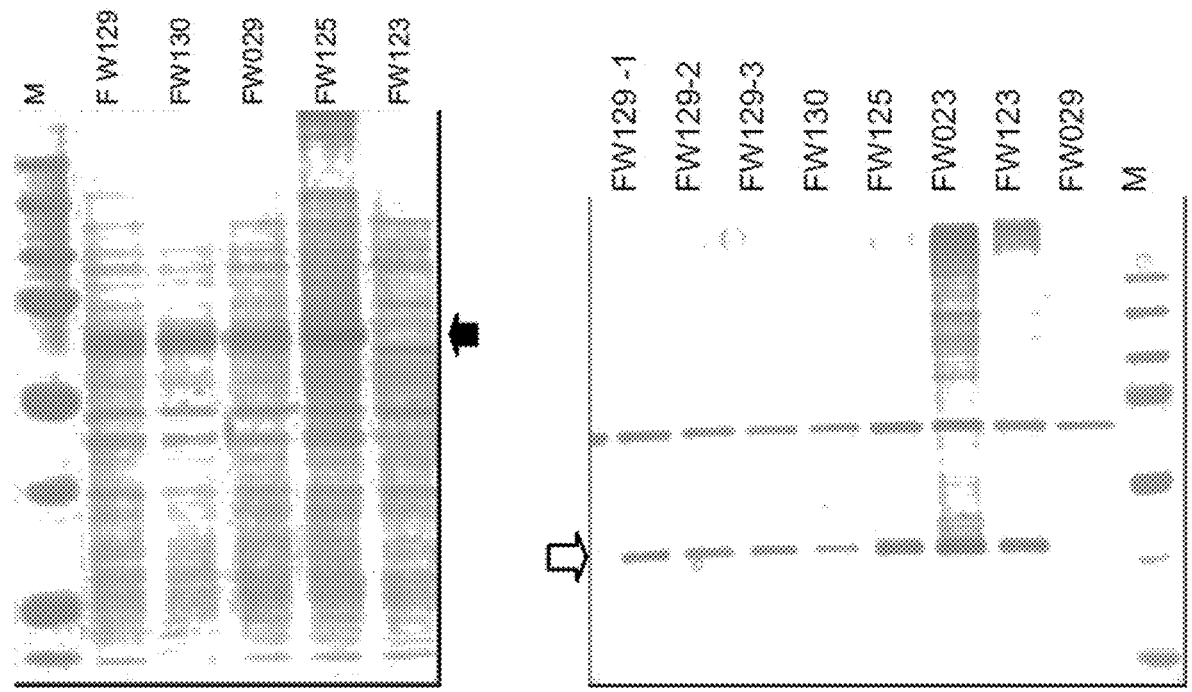
Fig. 4A
Fig. 4B

Fig. 5A: VP2 probe
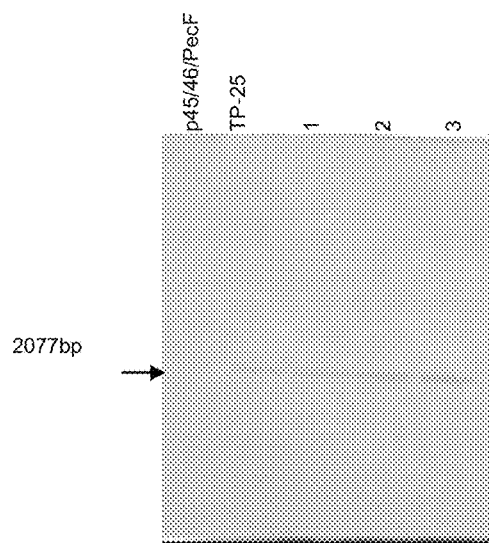
Fig. 5B: 44/45 probe
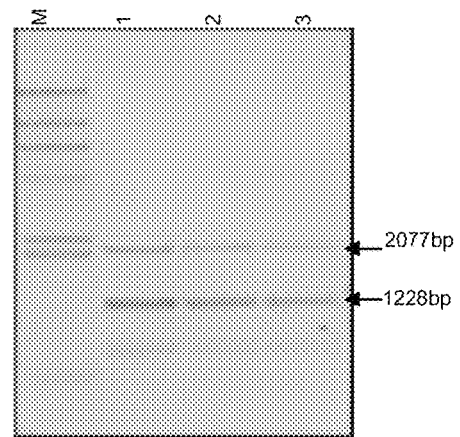
Fig. 5C: F probe
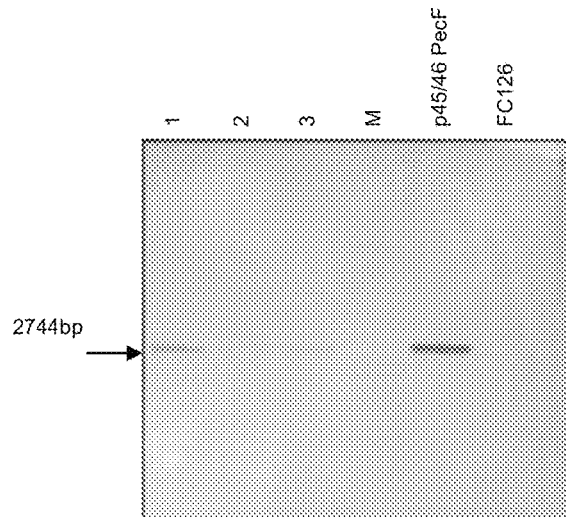
Fig. 5D: 45/46 probe
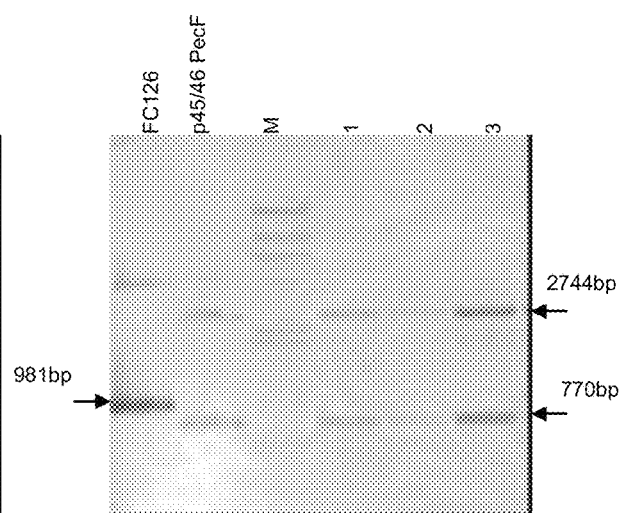

MULTIVALENT RECOMBINANT AVIAN HERPES VIRUSES AND VACCINES FOR IMMUNIZING AVIAN SPECIES

CROSS-REFERENCE TO RELATED APPLICATIONS

This application is a continuation of U.S. application Ser. No. 16/707,106, filed Dec. 9, 2019, now U.S. Pat. No. 11,123,425, which is a continuation of U.S. application Ser. No. 15/972,283, filed May 7, 2018, now U.S. Pat. No. 10,500,270, which is a continuation of U.S. application Ser. No. 14/388,268, filed Sep. 26, 2014, now U.S. Pat. No. 10,251,951, which is the national stage application of International Patent Application No. PCT/EP2013/056839, filed Mar. 29, 2013.

The Sequence Listing for this application is labeled "Seq-List.txt" which was created on May 15, 2018 and is 12 KB. The entire contents of the sequence listing is incorporated herein by reference in its entirety.

FIELD OF THE INVENTION

The present invention relates generally to the field of vaccine preparations. The present invention specifically relates to multivalent recombinant herpes viruses in which at least two foreign genes have been inserted, and their uses for simultaneously inducing a protective immunity against a plurality of avian diseases.

BACKGROUND OF THE INVENTION

Poultry meat and eggs are important food sources, whose consumption increases continually due to the growth of the human population and their great quality-price ratio. The recent epidemic of avian influenza focused the public opinion on poultry health as well as food safety and security. Poultry vaccine technology became a worldwide concern.

Viral vectors expressing pathogen proteins are commonly used as poultry vaccines against targeted pathogens. Vaccines including such viral vectors induce expression of foreign pathogen proteins within infected cells, and thereby induce corresponding T-cell immunity.

It is well known that all herpes viruses, including herpes virus of turkey (HVT) and Marek's disease virus (MDV), can permanently survive in the body of an infected animal in a state of latent or persistent infection. Consequently, recombinant herpes viruses, in which a foreign gene derived from a pathogen has been integrated, have been developed to be used as viral-vectored vaccines increasing the duration of immunity of an immunized animal.

The genomic structure of HVT, its widespread usage as a vaccine against MDV and its ability to remain persistent in chickens make this virus an attractive vector for producing recombinant poultry vaccines.

Vaccine preparations have been developed to achieve effective avian vaccinations, using recombinant herpes viruses which incorporate a gene encoding a foreign antigen. Such vaccine preparations allow vaccination against both MDV (the vector) and another avian disease, through the inserted foreign DNA sequence.

Although such vaccine preparations provide efficient results of vaccination of avian species against many fatal diseases, competition and immunosuppression between pathogens can occur when birds are injected with two or more recombinant herpes viruses, each harboring a different foreign antigen gene.

Therefore, multivalent recombinant herpes viruses (i.e., harboring at least two different antigen genes) for immunizing simultaneously against different diseases would be particularly studied. However, up to now, recombinant HVTs (rHVTs) expressing multiple foreign genes turned out to be unstable, and all or part of the foreign genes are deleted during repeated passaging in culture cells. Accordingly, such unstable multivalent virus vectors cannot be used as efficient vaccines.

Accordingly, there is a need for stable multivalent recombinant viral vectors, allowing the co-expression of the foreign genes in infected cells.

SUMMARY OF THE INVENTION

Work conducted by the applicant has led to the surprising finding that a set of particular insertion sites in a herpes virus genome can be used for stably inserting and expressing two or more antigen genes, thereby providing efficient multivalent viral vectors for avian vaccination. More particularly, applicant has found that a small number of insertion sites can be used simultaneously for incorporating distinct antigen genes, providing stable multivalent recombinant viral vectors.

Therefore, the present invention relates to a recombinant avian herpes virus which comprises at least two recombinant nucleotide sequences, each recombinant nucleotide sequence encoding and expressing an antigenic peptide in cells of avian species, wherein said at least two recombinant nucleotide sequences are inserted into distinct non-coding regions of the viral genome chosen among the region located between UL44 and UL45, the region located between UL45 and UL46, the region located between US10 and SORF3, and the region located between SORF3 and US2.

In a preferred embodiment, one recombinant nucleotide sequence is inserted in the region located between UL45 and UL46, and one recombinant nucleotide sequence is inserted in the region located between UL44 and UL45, between US10 and SORF3, or between SORF3 and US2. As illustrated in the application, such recombinant avian herpes virus constructs provide particularly stable and efficient expression of the two corresponding antigenic peptides in infected avian cells.

In particular, advantageously, the two or more recombinant nucleotide sequences are co-expressed in Chicken Embryo Fibroblast (CEF) cells, even after 10 or more passages, and preferentially even after 15 passages.

According to the invention, the recombinant nucleotide sequences are advantageously under the control of particular promoters. The promoters are preferentially chosen among the chicken beta-actin (Bac) promoter, the Pec promoter, the Murine Cytomegalovirus (mCMV) immediate-early (IE)1 promoter, Human Cytomegalovirus (Hcmv) promoter, the Simian virus (SV)40 promoter, and the Raus Sarcoma virus (RSV) promoter, or any fragments thereof which retain a promoter activity. Preferentially, each recombinant nucleotide sequence is under the control of a distinct promoter.

According to the invention, the foreign genes are advantageously chosen among an antigenic peptide of avian paramyxovirus type 1, and preferably the F protein of Newcastle disease virus (NDV), an antigenic peptide of Gumboro disease virus, preferentially the VP2 protein of the infectious bursal disease virus (IBDV), an antigenic peptide of the infectious laryngotracheitis virus (ILTV), preferentially the gB protein, an antigenic peptide of Mycoplasma galisepticum, preferentially the 40K protein, and an antigenic peptide of the *avian* influenza virus, preferentially a surface protein hemagglutinin (HA).

In a preferred embodiment, the recombinant *avian* herpes virus comprises a first recombinant nucleotide sequence encoding a first antigenic peptide inserted into the non-coding region located between UL44 and UL45, and a second recombinant nucleotide sequence encoding a second antigenic peptide inserted into the non-coding region located between UL45 and UL46, between US10 and SORF3, or between SORF3 and US2.

In another preferred embodiment, the recombinant *avian* herpes virus comprises a first recombinant nucleotide sequence encoding a first antigenic peptide inserted into the non-coding region located between UL45 and UL46, and a second recombinant nucleotide sequence encoding a second antigenic peptide inserted into the non-coding region located between US10 and SORF3, or between SORF3 and US2.

In further preferred embodiment, the recombinant *avian* herpes virus comprises a first recombinant nucleotide sequence encoding a first antigenic peptide inserted into the non-coding region located between US10 and SORF3, and a second recombinant nucleotide sequence encoding a second antigenic peptide inserted into the non-coding region located between SORF3 and US2.

A further object of the invention relates to a multivalent vaccine for immunizing *avian* species, such as poultry, which comprises an effective immunizing amount of recombinant *avian* herpes virus of the invention. This vaccine can be used for immunizing *avian* species, such as poultry.

A further object of the invention concerns an antiserum directed against *avian* herpes virus obtained by immunizing *avian* species with an effective amount of recombinant *avian* herpes virus of the invention and recovering the antiserum after bleeding the bird.

The invention further relates to a method of immunizing an *avian* comprising administering to said *avian* an effective immunizing amount of the vaccine according to the invention.

The invention further provides a vaccination kit for immunizing *avian* species which comprises an effective amount of the vaccine of the invention, and a means for administering said components to said species.

The invention may be used in any *avian*, for vaccination against any *avian* pathogen.

BRIEF DESCRIPTION OF THE DRAWINGS

FIG. 3 shows immunofluorescence staining of CEFs infected with double recombinant HVTs according to embodiments of the invention (FW129 and FW141) co-expressing NDV-F and IBDV-VP2 (rHVT/ND/IBD infected cells). Protein VP2 expression was detected by anti-VP2 Mab (R63) and Alexa Fluor 546. Protein F expression was detected by anti-F #35 rabbit serum and Alexa Fluor 488.

The results show that both cells infected with FW129 or FW141 express both the inserted NDV-F protein and the inserted IBDV-VP2 protein.

FIGS. 4A and 4B are Western blotting analyses showing the expression of VP2 protein and/or F protein in CEF cells infected with rHVTs of the invention. As shown in FIG. 4A, a protein band of 60 kilodaltons (kDa) was observed only in the lane with rHVT/ND/IBD infected cells, which was the expected size of the F protein (➡). There was no band in the lane of rHVT/44-45BacVP2 (FW123). As shown in FIG. 4B, VP2 protein was observed at 38-kilodaltons (kd) in the lanes of each rHVT/ND/IBD (⇨). On the contrary, there was no band in the lane of rHVT/45-46 PecF (FW029). The 38-kd is the mature VP2 protein (A. A. Azad et al., 1987, Virol. 161:145-152; K. J., Fahey et al., 1985, J. Gen. Virol. 66:1479-1488). Double rHVTs of the invention expressed both NDV-F and IBDV-VP2.

FIGS. 5A to 5D show results of a Southern blotting analysis for a genome structure check of purified FW129 (rHVT/45-46 pecF/44-45 Rsv VP2), indicating that double recombinant HVT/ND/IBD of the invention had the expected genomic structure. More precisely, the results of Southern blotting showed that:

a 2077-bp fragment was hybridized to a VP2 probe in the DNA from each double recombinant HVT FW129 (columns 1, 2 and 3, FIG. 5A). In contrast, no band was detected in p45/46Pec F (FIG. 5A).

a 2744-bp fragment was hybridized to an F probe in the DNA from each double recombinant HVT FW129 (columns 1, 2 and 3, FIG. 5C). No band was detected in the p45/46 SfiI.

2077-bp and 1228-bp fragments were hybridized to an IS44/45 probe in the DNA from each double recombinant HVT FW129 (columns 1, 2 and 3, FIG. 5B). No band was detected for the molecular marker ramda HindIII digest (column M, FIG. 5B).

2744-bp and 770-bp fragments were hybridized to an IS45/46 probe in the DNA from each double recombinant HVT FW129 (columns 1, 2 and 3, FIG. 5D).

Figure 6A:
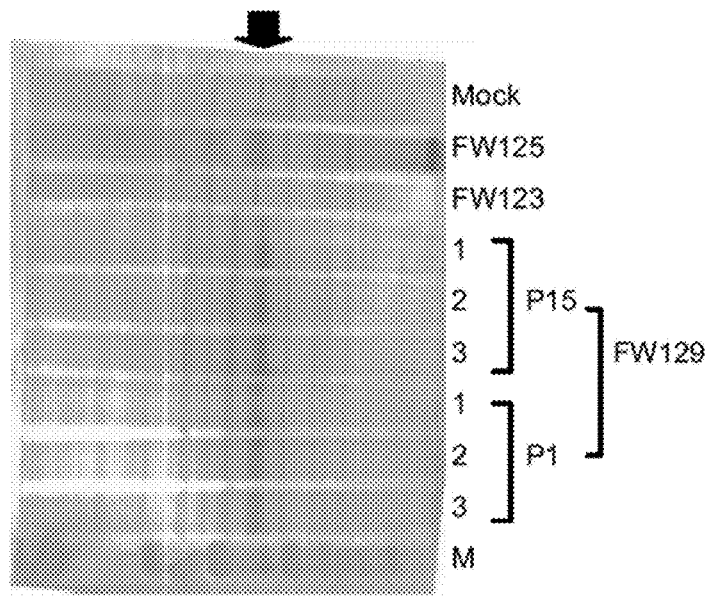
Figure 6B:
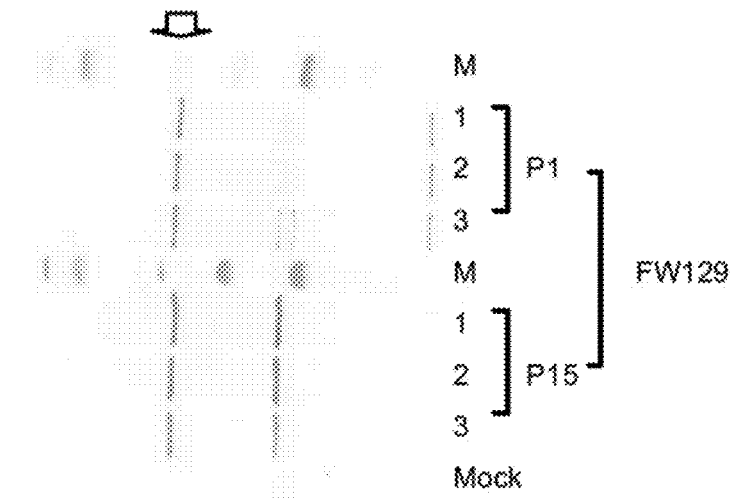

FIGS. 6A and 6B show results of a Western blotting analysis for a stability check of recombinant HVT FW129 in successive passages, indicating that after 15 passages F protein and VP2 protein were expressed stably in CEF infected with the rHVT FW129 of the invention.

FIGS. 7A to 7D show results of a Southern blotting analysis for a stability check of recombinant HVTs after 15 passages. (FIG. 7A) The results of Southern blotting show that a 2077-bp fragment was hybridized to a VP2 probe in the DNA from FW129. A 2334-bp fragment was hybridized to a VP2 probe in the DNA from FW130. In contrast, no band was detected in p45/46Pec F. (FIG. 7C) The results of Southern blotting show that a 2744-bp fragment was hybridized to an F probe in the DNA from each double recombinant HVT FW129 and FW130. No band was detected in the p45/46 SfiI. (FIG. 7B) The results of Southern blotting show that 2077-bp and 1228-bp fragments were hybridized to an IS44/45 probe in the DNA from FW129, and that 2334-bp and 1022-bp fragments were hybridized to an IS44/45 probe in the DNA from FW130. A 1350-bp fragment was hybridized to an IS44/45 probe in p45/46 PecF, which contained no gene at the IS44/45 site. (FIG. 7D) The results of Southern blotting show that 2744-bp and 770-bp fragments were hybridized to an IS45/46 probe in the DNA from each double recombinant HVT FW129 and FW130. A Southern blot with a 44/45 probe and 45/46 probe showed the VP2 gene or F gene stably maintained at the insertion site 44/45 or 45/46 respectively in FW129 and FW130. These results indicate that after 15 passages F protein and VP2 protein were expressed stably in CEF infected with the rHVT FW129 of the invention.

Figure 8:
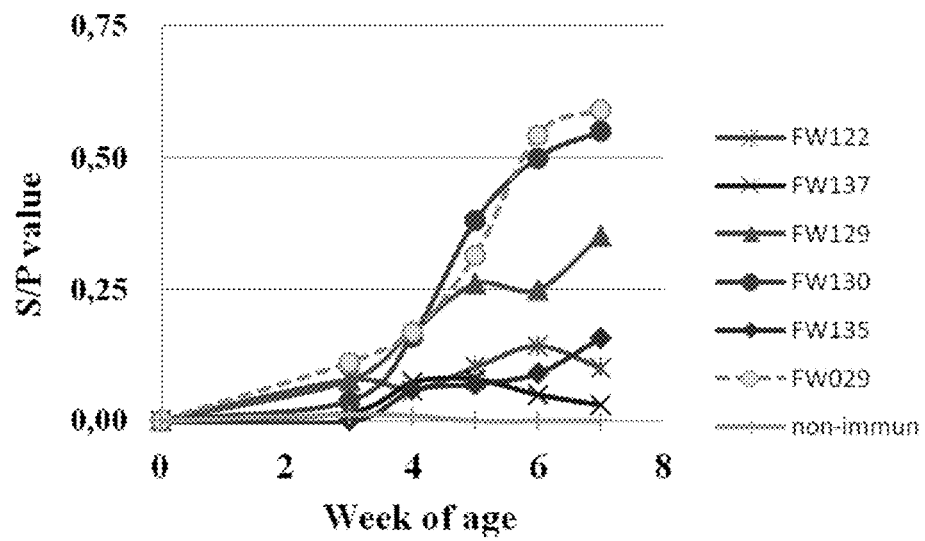
Figure 8B:
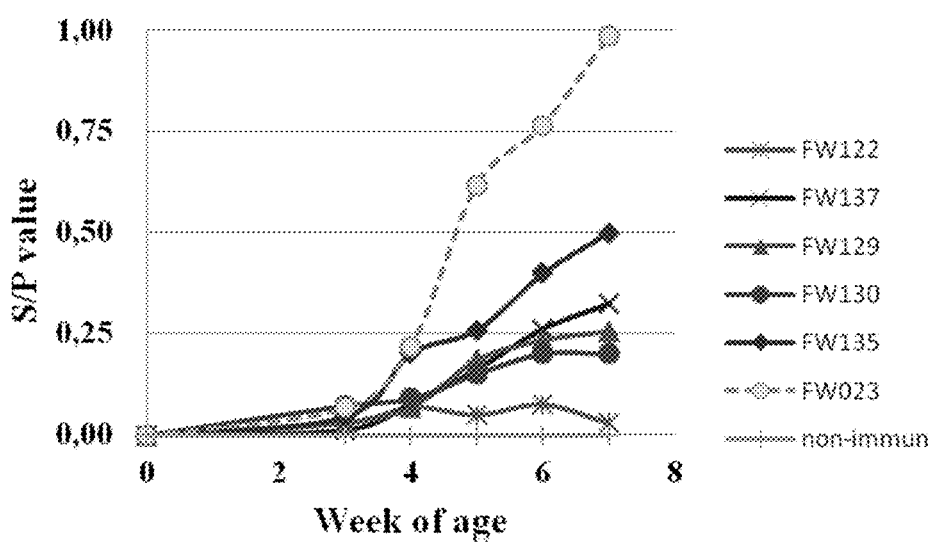

FIGS. 8A and 8B show comparative results of anti-NDV titers (FIG. 8A) and anti-IBDV titers (FIG. 8B) obtained from chicken inoculated with double recombinant HVTs (FW122, FW137, FW129, FW130, and FW135), compared to titers obtained from chicken inoculated with single recombinant HVTs (FW029 and FW023 respectively).

DETAILED DESCRIPTION OF THE INVENTION

The present invention generally relates to multivalent recombinant herpes viruses and their use for immunizing avian species against at least two diseases in the same time. According to the invention, foreign DNA sequences are inserted in particular insertion sites within the rHV genome, providing stable and efficient constructs suitable for use in vaccine compositions or methods.

The present disclosure will be best understood by reference to the following definitions:

Definitions

In the context of the invention, the term "reconstructed" or "recombinant", in relation to a sequence, designates a sequence, nucleic acid or unit which does not exist naturally and/or which has been engineered using recombinant DNA technology (also called gene cloning or molecular cloning).

The term "recombinant" in relation to a herpes virus refers to a herpes virus whose genome has been modified by insertion of at least one heterologous nucleic acid, i.e., a nucleic acid (e.g., DNA) which is not found naturally in the genome of the herpes virus, or which is found naturally in said genome but in a different form or at a different position. It will be understood that the recombinant herpes virus can be manufactured by a variety of methods, and, once made, can be reproduced without use of further recombinant DNA technology. The structure of the "recombinant herpes virus" is therefore described in terms of DNA insertion.

In the present description, the terms "nucleic acid", "nucleic sequence," and "nucleotide sequence" are used interchangeably and refer to a nucleic acid molecule having a determined sequence, which may be deoxyribonucleotides and/or ribonucleotides. The nucleotide sequence may be first prepared by, e.g., recombinant, enzymatic and/or chemical techniques, and subsequently replicated in a host cell or an in vitro system. A nucleotide sequence preferentially comprises an open reading frame encoding a peptide. The nucleotide sequence may contain additional sequences such as a transcription terminator, a signal peptide, an IRES, an intron, etc. Preferably, an open reading frame in a recombinant nucleic acid does not contain an intron.

The term "untranslated region" as used herein refers to a region of nucleotides that has no ORF and does not define an amino acid sequence of protein to be expressed by translation, or a region of nucleotides in which the ORF is not involved in any of transcription, translation, or protein expression.

The term "avian species" is intended to encompass all kinds of avians such as birds of the class of Ayes, i.e., vertebrate animals which are feathered, winged, bipedal, endothermic and egg-laying. In the context of the invention, avians or avian species refer more particularly to birds with economical and/or agronomical interests, such as poultry (such as chickens and turkeys), waterfowl poultry (such as ducks and geese) and ornamental birds (such as swans and psittacines).

The term "vaccine" as used herein designates an agent which may be used to cause, stimulate or amplify an immune response in an organism.

Viruses

Viruses for use in the present invention are those that belong generally to the genus of avian herpes viruses.

For example, avian herpes viruses for use in the present invention include, but are not limited to, a herpes virus of turkeys (HVT), a serotype 2 Marek's disease virus, preferably the SB1 strain of the serotype 2 Marek's disease virus, or a serotype 1 Marek's disease virus, preferably the CVI988/Rispens strain of the serotype 1 Marek's disease virus. Preferred herpes viruses of the invention are derived from serotypes or strains that are non-pathogenic to targeted avian species.

Multivalent Recombinant Avian Herpes Viruses

An object of the invention relates to recombinant avian herpes viruses suitable for immunizing avian species against at least two diseases, with improved stability through passages. Particular insertion sites have been identified by the inventors which, in combination, provide improved stability for foreign antigen genes.

An object of the invention therefore relates to a recombinant avian herpes virus which comprises at least two recombinant nucleotide sequences, each recombinant nucleotide sequence encoding a distinct antigenic peptide, wherein said at least two recombinant nucleotide sequences are inserted into distinct non-coding regions of the viral genome chosen among the region located between UL44 and UL45, the region located between UL45 and UL46, the region located between US10 and SORF3, and the region located between SORF3 and US2.

The location of the quoted non-coding regions is known in the art and can be found, e.g., in Kingham et al. ("*The genome of herpesvirus of turkeys: comparative analysis with Marek's disease viruses*"—Journal of General Virology (2001) 82, 1123-1135).

For example, by reference to an FC126 complete genome (GenBank: AF291866.1), the region located between UL44 and UL45 corresponds to nucleotides 94243-94683 of the HVT genome, the region located between UL45 and UL46 corresponds to nucleotides 95323-95443 of the HVT genome, the region located between US10 and SORF3 corresponds to nucleotides 138688-138825 of the HVT genome, and the region located between SORF3 and US2 corresponds to nucleotides 139867-140064 of the HVT genome.

The nucleic acid of interest for insertion into the genome of the herpes virus may be homologous or heterologous with respect to the herpes virus. The nucleic acid typically encodes an antigen from a pathogen and may be derived or obtained from any pathogenic organism capable of causing an infection in avian species. Typically, the cloned nucleic acids are derived from pathogens which cause diseases that have an economic impact on the poultry industry. Examples of pathogens that cause infection in avians include viruses, bacteria, fungi, protozoa, etc.

The homologous or heterologous nucleotide sequence for insertion into the viral genome may thus be any sequence coding for an antigenic peptide of a bird pathogenic agent. The nucleic acid sequence according to the present invention can be derived from any source, e.g., viral, prokaryotic, eukaryotic or synthetic. Typically, the nucleotide sequences encode an immunogenic peptide of a pathogen, and preferably represent surface proteins, secreted proteins or structural proteins of said pathogen, or fragments thereof.

The nucleotide sequence may encode for example an antigenic peptide derived from *avian* influenza virus, *avian* paramyxovirus type 1, also called Newcastle disease virus (NDV), *avian* metapneumovirus, Marek's disease virus, Gumboro disease virus, also called infectious bursal disease virus (IBDV), infectious laryngotracheitis virus (ILVT), infectious bronchitis virus (IBV), *Escherichia coli, Salmonella* species, *Pasteurella multocida, Riemerella anatipestifer, Ornithobacterium rhinotracheale, Mycoplasma galisepticum, Mycoplasma synoviae, Mycoplasma* microorganisms infecting *avian* species or coccidia.

Preferentially, the nucleotide sequences inserted into the viral genome are chosen among the F protein of NDV, the VP2 protein of IBDV, the gB protein of ILTV, the 40K, protein of *Mycoplasma galisepticum*, and the surface protein hemagglutinin (HA) of the *avian* influenza virus.

Various combinations of antigenic peptides may present great interest, depending on several factors, such as *avian* species, rearing country, rearing conditions, etc.

For example, in an embodiment, the multivalent recombinant *avian* herpes virus of the invention incorporates into its genome the nucleotide sequence coding for the F protein of NDV and the nucleotide sequence coding for the VP2 protein of IBDV.

According to a particular embodiment, three or more nucleotide sequences may be inserted into the viral genome.

The recombinant herpes virus of the invention can express two or more antigens from the same pathogen.

The homologous or heterologous nucleotide sequences coding for the antigens of interest may be operably linked to a promoter and further inserted into the viral genome. The promoter used may be either a synthetic or natural, endogenous or heterologous promoter.

The promoter is not limited as long as it can effectively function in cells of birds infected with rHVT. Hence the choice of a promoter extends to any eukaryotic, prokaryotic or viral promoter capable of directing gene transcription in *avian* cells infected by the rHVT.

Preferentially, the promoters are chosen among the chicken beta-actin (Bac) promoter, the Pec promoter, the Murine Cytomegalovirus (mCMV) IE1 promoter, the Human Cytomegalovirus (Hcmv) promoter, the Simian virus (SV)40 promoter, and the Raus Sarcoma virus (RSV) promoter, or any fragments thereof which retain a promoter activity.

The nucleic acid sequence of a chicken Bac promoter is shown in SEQ ID NO: 1, the sequence of a Pec promoter is shown in SEQ ID NO: 2, the sequence of an mCMV IE1 promoter is shown in SEQ ID NO: 3, the sequence of an Hcmv promoter is shown in SEQ ID NO: 4, the sequence of an SV40 promoter is shown in SEQ ID NO: 5, and the sequence of an RSV promoter is shown in SEQ ID NO: 6.

It should be noted that variants of such sequences encoding functional promoters are known and/or can be designed/tested by the skilled artisan, for use in the instant invention.

In a preferred recombinant herpes virus of the invention, at least one of the nucleic acids comprises a Pec or Bac promoter to drive expression of the antigenic peptide.

Multivalent Construction

Gene cloning and plasmid construction are well known to a person of ordinary skill in the art and may be essentially performed by standard molecular biology techniques (*Molecular Cloning: A Laboratory Manual*, 3rd Edition, Cold Spring Harbor Laboratory Press, Woodbury, N.Y. 2001).

In order to construct a multivalent recombinant herpes virus of the present invention, initially, the herpes virus is propagated in a suitable host cell and then the genomic DNA is obtained. The host and the conditions for propagating the virus are selected as appropriate. As host cells, cells derived from chicken are preferred, and CEF (chick embryo fibroblast), chicken kidney cells, and the like can be used. They may be cultured in a culture medium such as Eagle's MEM, Leibowitz-L-15/McCoy 5A (1:1 mixture) culture medium at about 37° C. for 3 to 4 days.

DNA is extracted from the virus-infected cells cultured as above according to a conventional method. After protein is denatured in the lysis buffer and removed, DNA is extracted with phenol and ethanol.

Typically, the recombinant viruses may be prepared by homologous recombination between the viral genome and a construct (e.g., a plasmid) comprising the nucleic acid to be inserted, flanked by nucleotides from the insertion site to allow recombination.

Plasmid with Insertion Site Sequence

One possibility to insert a foreign gene in one of the untranslated regions of the viral genome according to the invention may be to first clone a sequence containing the targeted untranslated region into a plasmid, or other suitable vector. According to the invention, such sequence is chosen among the sequence of the region located between UL44 and UL45, the sequence of the region located between UL45 and UL46, the sequence of the region located between US10 and SORF3, and the sequence of the region located between SORF3 and US2.

Examples of plasmids comprise pBR322, pBR325, pBR327, pBR328, pUC18, pUC19, pUC7, pUC8, and pUC9, examples of phages comprise lambda phage and M13 phage, and an example of cosmids comprises pHC79.

The untranslated region sequence is integrated into the plasmid according to a conventional cloning method. The insertion region sequences are preferably of sufficient length so that, upon insertion of the nucleic acid, the sequences which flank the nucleic acid are of appropriate length so as to allow in vivo homologous recombination with the viral genome. Preferably, the flanking sequences shall have at least approximately 50 nucleotides in length.

In order to insert one or more foreign sequence(s) into the untranslated region, mutation may be carried out at a specific site of the untranslated region to make a new cleavage site for restriction enzymes. A method of carrying out mutation may be a conventional method, and a method commonly used by a person skilled in the art such as in vitro mutagenesis and PCR can be used. Thus, in the PCR method, a mutation such as the deletion, replacement, or addition of 1 to 2 nucleotides in the PCR primer is carried out, and the primer is then used to create a mutation.

Plasmid Further Containing Targeted Foreign Nucleotide Sequence(s)

The nucleotide and promoter sequences, for insertion into the virus, are further inserted into the insertion region of the viral genome in the plasmid.

More precisely, the nucleotide and promoter sequences are introduced into a fragment of genomic herpes virus DNA containing insertion region sequences, subcloned in the plasmid.

If desired, a plasmid can be prepared which contains two or more foreign nucleic acid sequences, e.g., derived from the same or different pathogens, said sequences being flanked by insertion region sequences as described herein.

Viral Genome Comprising a Foreign Nucleotide Sequence in an Insertion Site

Plasmids in which at least one nucleotide sequence has been inserted into the untranslated region obtained as above may be introduced into an HVT-infected cell or HVT genome-transfected cell using electroporation, calcium phosphate, a lipofectin-based method or the like. When the amount of the plasmid to be introduced is in the range of 0.1 to 1000 μg, the efficiency of generation of recombinant viruses by recombination between the homologous regions of HVT-DNA and the plasmid becomes high in cells.

Production of the Multivalent Recombinant Herpes Virus

The multivalent of the invention may be obtained by co-transfecting in the same cell culture a plasmid containing, as described above, an insertion site sequence in which is integrated a foreign nucleotide sequence, and a recombinant herpes virus containing, as described above, the same insertion site free of the foreign nucleotide sequence and a second insertion site in which is integrated a distinct foreign nucleotide sequence. This co-transfection results in the recombination of the plasmid DNA into the viral genome.

Otherwise, the multivalent of the invention may be obtained by co-transfecting in the same cell culture two plasmids each containing a distinct insertion site sequence in which is integrated a distinct foreign nucleotide sequence, and a herpes virus containing, as described above, the same insertion sites free of the foreign nucleotide sequence. The co-transfection results in the recombination of both plasmid DNAs into the viral genome.

The resulting multivalent recombinant virus may be selected genotypically or phenotypically using known techniques of selection, e.g., by hybridization, detecting enzyme activity encoded by a gene co-integrated along with the recombinant nucleic acid sequences or detecting the antigenic peptide expressed by the recombinant herpes virus immunologically. The selected recombinant herpes virus can be cultured on a large scale in cell cultures after which recombinant herpes virus-containing peptides can be collected.

Preferred Multivalent Constructions

It is an object of the invention to propose multivalent recombinant herpes viruses which present at least two foreign nucleotide sequences each being inserted in a particular insertion site, in suitable manner for encoding and expressing the corresponding antigenic peptides in *avian* cells.

Among the plurality of possible embodiments based on the combinations of the targeted insertion sites and the preferred recombinant nucleotide sequences, and optionally the preferred promoters, the Applicant has surprisingly found that particular combinations present a high level of stability, allowing their use for preparing improved multivalent vaccines.

Based on this noticing, it is a purpose of the invention to propose specific multivalent recombinant *avian* herpes viruses with a high level of stability.

Preferred multivalent recombinant *avian* herpes viruses of the invention comprise two recombinant nucleotide sequences, each recombinant nucleotide sequence encoding a distinct antigenic peptide and being inserted into a distinct non-coding region of the viral genome chosen among the region located between UL44 and UL45, the region located between UL45 and UL46, the region located between US10 and SORF3, and the region located between SORF3 and US2.

Preferred antigenic peptides of the invention are chosen among the F protein of NDV, the VP2 protein of IBDV, the gB protein of ILTV, the 40K protein of *Mycoplasma galisepticum*, and the surface protein HA of the *avian* influenza virus.

Advantageously, the promoters used with nucleotide sequences inserted in the insertion site between UL44 and UL45 are chosen among the Pec promoter, the mCMV IE1 promoter, the Hcmv promoter, the SV40 promoter, and the RSV promoter, or any fragments thereof which retain a promoter activity. Indeed, applicant has surprisingly found that the Bac promoter inserted between UL44 and UL45 does not allow stable expression of a foreign gene. However, the Bac promoter inserted in the region between UL45 and UL46 does allow stable expression.

According to a first embodiment, the recombinant *avian* herpes virus comprises, inserted between UL45 and UL46, a recombinant nucleotide sequence encoding the F protein of NDV or a fragment thereof, preferentially under the control of the Pec promoter, and, inserted between UL44 and UL45, a recombinant nucleotide sequence encoding the VP2 protein of IBDV or a fragment thereof, preferentially under the control a SV40 promoter (FW130).

According to a second embodiment, the recombinant *avian* herpes virus comprises in the insertion site between UL45 and UL46 a recombinant nucleotide sequence encoding the F protein of NDV or a fragment thereof, preferentially under the control of the Pec promoter, and in the insertion site between UL44 and UL45 a recombinant nucleotide sequence encoding the VP2 protein of IBDV or a fragment thereof, preferentially under the control of the RSV promoter (FW129).

According to a third embodiment, the recombinant *avian* herpes virus comprises in the insertion site between UL45 and UL46 a recombinant nucleotide sequence encoding the F protein of NDV, or a fragment thereof, preferentially under the control of the Pec promoter and in the insertion site between UL44 and UL45 a recombinant nucleotide sequence encoding the VP2 protein of IBDV or a fragment thereof, preferentially under the control of the mCMV IE1 promoter (FW141).

According to a fourth embodiment, the recombinant *avian* herpes virus comprises in the insertion site between UL45 and UL46 a recombinant nucleotide sequence encoding the F protein of NDV, or a fragment thereof, preferentially under the control of the Pec promoter and in the insertion site between SORF3 and US2 a recombinant nucleotide sequence encoding the VP2 protein of IBDV or a fragment thereof, preferentially under the control of the mCMV IE1 promoter (FW144).

According to a fifth embodiment, the recombinant *avian* herpes virus comprises in the insertion site between UL45 and UL46 a recombinant nucleotide sequence encoding the F protein of NDV or a fragment thereof, preferentially under the control of the Pec promoter, and in the insertion site between SORF3 and US2 a recombinant nucleotide sequence encoding the VP2 protein of IBDV or a fragment thereof, preferentially under the control of the Bac promoter (FW146).

According to a sixth embodiment, the recombinant *avian* herpes virus comprises in the insertion site between UL44 and UL45 a recombinant nucleotide sequence encoding the F protein of NDV or a fragment thereof, preferentially under the control of the Pec promoter, and in the insertion site between UL45 and UL46 a recombinant nucleotide sequence encoding the VP2 protein of IBDV or a fragment thereof, preferentially under the control of the mCMV IE1 promoter (FW143).

According to a seventh embodiment, the recombinant *avian* herpes virus comprises in the insertion site between UL44 and UL45 a recombinant nucleotide sequence encoding the F protein of NDV or a fragment thereof, preferentially under the control of the mCMV IE1 promoter, and in the insertion site between UL45 and UL46 a recombinant nucleotide sequence encoding the VP2 protein of IBDV or a fragment thereof, preferentially under the control of the Bac promoter (FW142).

According to an eighth embodiment, the recombinant *avian* herpes virus comprises in the insertion site between SORF3 and US2 a recombinant nucleotide sequence encoding the F protein of NDV or a fragment thereof, preferentially under the control of the Pec promoter, and in the insertion site between UL45 and UL46 a recombinant nucleotide sequence encoding the VP2 protein of IBDV or a fragment thereof, preferentially under the control of the Bac promoter (FW147).

According to a ninth embodiment, the recombinant *avian* herpes virus comprises in the insertion site between UL45 and UL46 a recombinant nucleotide sequence encoding the VP2 protein of IBDV or a fragment thereof, preferentially under the control of the Bac promoter, and in the insertion site between SORF3 and US2 a recombinant nucleotide sequence encoding the F protein of NDV or a fragment thereof, preferentially under the control of the mCMV IE1 promoter (FW145).

According to a tenth embodiment, the recombinant *avian* herpes virus comprises in the insertion site between UL45 and UL46 a recombinant nucleotide sequence encoding the VP2 protein of IBDV or a fragment thereof, preferentially under the control of the Bac promoter, and in the insertion site between SORF3 and US2 a recombinant nucleotide sequence encoding the F protein of NDV or a fragment thereof, preferentially under the control of the SV40 promoter (FW149).

According to an eleventh embodiment, the recombinant *avian* herpes virus comprises in the insertion site between UL45 and UL46 a recombinant nucleotide sequence encoding the F protein of NDV or a fragment thereof, preferentially under the control of the SV40 promoter, and in the insertion site between SORF3 and US2 a recombinant nucleotide sequence encoding the VP2 protein of IBDV or a fragment thereof, preferentially under the control of the Bac promoter (FW148).

According to a twelfth embodiment, the recombinant *avian* herpes virus comprises in the insertion site between UL45 and UL46 a recombinant nucleotide sequence encoding the F protein of NDV or a fragment thereof, preferentially under the control of the Pec promoter, and in the insertion site between US10 and SORF3 a recombinant nucleotide sequence encoding the VP2 protein of IBDV or a fragment thereof, preferentially under the control of the mCMV IE1 promoter (FW153).

According to a thirteenth embodiment, the recombinant *avian* herpes virus comprises in the insertion site between UL45 and UL46 a recombinant nucleotide sequence encoding the F protein of NDV or a fragment thereof, preferentially under the control of the Pec promoter, and in the insertion site between US10 and SORF3 a recombinant nucleotide sequence encoding the VP2 protein of IBDV or a fragment thereof, preferentially under the control of the Bac promoter (FW154).

According to a fourteenth embodiment, the recombinant *avian* herpes virus comprises in the insertion site between UL5 and UL46 a recombinant nucleotide sequence encoding the VP2 protein of IBDV or a fragment thereof, preferentially under the control of the Bac promoter, and in the insertion site between US10 and SORF3 a recombinant nucleotide sequence encoding the F protein of NDV or a fragment thereof, preferentially under the control of the mCMV IE1 promoter (FW155).

According to a fifteenth embodiment, the recombinant *avian* herpes virus comprises in the insertion site between UL45 and UL46 a recombinant nucleotide sequence encoding the VP2 protein of IBDV or a fragment thereof, preferentially under the control of the Bac promoter, and in the insertion site between US10 and SORF3 a recombinant nucleotide sequence encoding the F protein of NDV or a fragment thereof, preferentially under the control of the Pec promoter (FW156).

According to a sixteenth embodiment, the recombinant *avian* herpes virus comprises in the insertion site between US10 and SORF3 a recombinant nucleotide sequence encoding the F protein of NDV or a fragment thereof, preferentially under the control of the Pec promoter, and in the insertion site between SORF3 and US2 a recombinant nucleotide sequence encoding the VP2 protein of IBDV or a fragment thereof, preferentially under the control of the mCMV IE1 promoter (FW157).

According to a seventeenth embodiment, the recombinant *avian* herpes virus comprises in the insertion site between US10 and SORF3 a recombinant nucleotide sequence encoding the F protein of NDV or a fragment thereof, preferentially under the control of the mCMV IE1 promoter, and in the insertion site between SORF3 and US2 a recombinant nucleotide sequence encoding the VP2 protein of IBDV or a fragment thereof, preferentially under the control of the Bac promoter (FW158).

According to an eighteenth embodiment, the recombinant *avian* herpes virus comprises in the insertion site between US10 and SORF3 a recombinant nucleotide sequence encoding the VP2 protein of IBDV or a fragment thereof, preferentially under the control of the Bac promoter, and in the insertion site between SORF3 and US2 a recombinant nucleotide sequence encoding the F protein of NDV or a fragment thereof, preferentially under the control of the mCMV IE1 promoter (FW159).

According to a nineteenth embodiment, the recombinant *avian* herpes virus comprises in the insertion site between US10 and SORF3 a recombinant nucleotide sequence encoding the VP2 protein of IBDV or a fragment thereof, preferentially under the control of the mCMV IE1 promoter, and in the insertion site between SORF3 and US2 a recombinant nucleotide sequence encoding the F protein of NDV or a fragment thereof, preferentially under the control of the Pec promoter (FW160).

According to a twentieth embodiment, the recombinant *avian* herpes virus comprises in the insertion site between UL45 and UL46 a recombinant nucleotide sequence encoding the VP2 protein of IBDV or a fragment thereof, preferentially under the control of the mCMV IE1 promoter, and in the insertion site between US10 and SORF3 a recombinant nucleotide sequence encoding the F protein of NDV or a fragment thereof, preferentially under the control of the Pec promoter (FW161).

Cell Cultures

The resulting recombinant viruses of the present invention may be propagated in cell cultures in which said recombinant virus can propagate and grow. After required growth of the viruses is achieved the cells may be detached from the wells using a scraper or with trypsin and the infected cells may be separated from the supernatant by centrifugation.

In preferred embodiments of the invention, CEF, embryonated egg, chicken kidney cells, and the like may be used as the host cells for the propagation of recombinant herpes viruses. Multivalent recombinant viruses of the present invention may be cultured in a culture medium such as Eagle's MEM, Leibowitz-L-15/McCoy 5A (1:1 mixture) culture medium at about 37° C. for 3 to 4 days. The infected cells thus obtained are suspended in a culture medium containing 10% dimethyl sulfoxide (DMSO) and stored frozen under liquid nitrogen.

Advantageously, the recombinant multivalent herpes viruses of the invention present a high level of stability through passages, which corresponds to a coexpression of the recombinant nucleotide sequences in cells of *avian* species even after 10 or more passages. In the context of the invention a "passage" or "cell passaging" means a culture of cells in suitable conditions for allowing their growth and keeping them alive until they are 90% to 100% confluent. The passaging step consists of transferring a small number of cells of the previous confluent culture into a new culture medium. An aliquot of the previous confluent culture, containing a few cells, may be diluted in a large volume of fresh medium. In case of adherent cultures, cells may first be detached, for example by using a mixture of trypsin and EDTA, or any suitable enzyme, before using a few number of detached cells for seeding a new culture medium.

According to preferred embodiments of the invention, CEF cells transfected with recombinant *avian* herpes viruses of the invention still coexpress the corresponding antigenic peptides after at least 10 passages. In other words, CEF cells resulting from 10 or more passages of CEF cells transfected with recombinant *avian* herpes viruses of the invention, and more particularly resulting from 15 passages, still contain the foreign nucleotide sequences of the recombinant *avian* herpes virus used for the initial cell transfection and express the at least two corresponding antigenic peptides. In the context of the invention, one considers that cells of a said passage still express the antigenic peptides if the level of production is greater than 80% of the level of production of the first passage, and preferentially greater than 85%.

Multivalent Vaccine Compositions

The invention also relates to a multivalent vaccine for immunizing *avian* species, such as poultry, which comprises an effective immunizing amount of a multivalent recombinant *avian* herpes virus of the invention.

Preferentially, vaccines of the invention are able to cause or stimulate or amplify immunity against at least two pathogens chosen among *avian* paramyxovirus type 1, Gumboro disease virus, the infectious laryngotracheitis virus, *Mycoplasma galisepticum*, and the *avian* influenza virus.

Vaccines of the invention comprise an immunologically effective amount of a multivalent recombinant herpes virus as described above, in a pharmaceutically acceptable vehicle.

A multivalent recombinant herpes virus according to the invention may preferably be used as a live vaccine although other alternatives like inactivated vaccines or attenuated vaccines are well within the skill of a person skilled in the art.

The vaccine according to the present invention may further comprise a suitable solvent, such as an aqueous buffer or a phosphate buffer. Preferably, the vaccine also comprises additives. Additives of the present invention may be obtained from any of a number of sources including various proteins and peptides derived from animals (e.g., hormones, cytokines, co-stimulatory factors), novel nucleic acids derived from viruses and other sources (e.g., double-stranded RNA, CpG), and the like, which are administered with the vaccine in an amount sufficient to enhance the immune response. In addition, any number of combinations of the aforementioned substances may provide an immunopotentiation effect, and therefore can form an immunopotentiator of the present invention.

The vaccines of the present invention may further be formulated with one or more further additives to maintain isotonicity, physiological pH and stability, for example, a buffer such as physiological saline (0.85%), phosphate-buffered saline (PBS), a citrate buffer, Tris(hydroxymethyl aminomethane (TRIS), Tris-buffered saline and the like, or an antibiotic, for example, neomycin or streptomycin, etc.

The route of administration can be any route including oral, ocular (e.g., by eyedrop), oculo-nasal administration using aerosol, intranasal, cloacal in feed, in water, or by spray, in ovo, topically, or by injection (e.g., intravenous, subcutaneous, intramuscular, intraorbital, intraocular, intradermal, and/or intraperitoneal) vaccination. The skilled person will easily adapt the formulation of the vaccine composition for each type of route of administration.

Each vaccine may contain a suitable dose sufficient to elicit a protective immune response in *avian* species. Optimization of such dose is well known in the art. The amount of antigen per dose may be determined by known methods using antigen/antibody reactions, for example by the ELISA method.

The vaccines of the invention can be administered as single doses or in repeated doses, depending on the vaccination protocol.

The vaccines of the present invention are further advantageous in that they confer to bird species up to 80% protection against the targeted *avian* pathogens after 3 weeks of vaccination.

The present invention further relates to the use of the vaccine as described above for immunizing *avian* species, such as poultry, and to a method of immunizing *avian* species by administering an immunologically effective amount of the vaccine according to the invention. The vaccine may be advantageously administered intradermally, subcutaneously, intramuscularly, orally, in ovo, by mucosal administration or via oculo-nasal administration.

The present invention further relates to vaccination kits for immunizing *avian* species which comprise an effective amount of the multivalent vaccine as described above and a means for administering said components to said species. For example, such a kit comprises an injection device filled with the multivalent vaccine according to the invention and instructions for intradermic, subcutaneous, intramuscular, or in ovo injection. Alternatively, the kit comprises a spray/aerosol or eyedrop device filled with the multivalent vaccine according to the invention and instructions for oculo-nasal, oral or mucosal administration.

The present invention will now be explained in more detail with reference to the following experiments and examples, but it must not be construed that the present invention is limited by these experiments and examples.

Experiments

In the experiments, several recombinant herpes viruses (monovalent or multivalent according to the invention) have been used, designated as follows (HVT/first insertion site-first foreign gene/second insertion site-second foreign gene):
FW122: HVT/45-46 Hcmv VP2 Bac F
FW123: HVT/44-45 Bac VP2
FW125: HVT/45-46 Bac F/44-45 Hcmv VP2

FW129: HVT/45-46 PecF/44-45 Rsv VP2
FW130: HVT/45-46 PecF/44-45 SV40 VP2
FW135: HVT/45-46 sv40 F/44-45 Bac VP2
FW137: HVT/45-46 Pec F sv40 VP2
FW141: HVT/45-46 PecF/44-45 mCMV IE1 VP2
FW142: HVT/45-46 Bac VP2/44-45 mCMV IE1 F
FW144: HVT/45-46 Pec F/87-88 mCMV IE1 VP2
FW145: HVT/45-46 Bac VP2/87-88 mCMV IE1 F
FW023: HVT/45-46 Bac VP2
FW029: HVT/45-46 Pec F

Experiment 1: Construction of Homology Vectors

The plasmid construction was essentially performed by the standard molecular biology techniques (Molecular Cloning: A Laboratory Manual, 3rd Edition, Cold Spring Harbor Laboratory, Cold Spring Harbor, N.Y. 2001). DNA restriction fragments were electrophoresed on agarose gels and purified with the Plasmid Plus Midi Kit (QIAGEN, Cat 12945).

Construction of p44/45d46Sfi

Based on the information of the gC homologue (gCh) gene of MDV serotype 1 (Coussens et al., J. Virol. 62:2373-2379, 1988) and its adjacent BamHI-B fragment (Japanese Unexamined Patent Publication No. H6-292583), a DNA fragment having an SfiI site between two ORFs, UL44h and UL45h, was prepared by PCR and cloned into pUC18. First, HVT DNA was prepared from CEF cells infected with the HVT FC126 strain according to the method of Lee et al. (J. Gen. Virol., 51:245-253, 1980). Using the obtained HVT DNA as a template, PCR was performed with two pairs of primers.

The first pair was SEQ ID NO: 7 (5'-CCCCGAATT-CATGGAAGAAATTTCC-3') and SEQ ID NO: 8 (5'-CGCGGGCCAATAAGGCCAACATCGGGACGTA-CATC-3').

The second pair was SEQ ID NO: 9 (5'-GCGCGGCCT-TATTGGCCTTAAATAC CGCGTTTGGAG-3') and SEQ ID NO: 10 (5'-CCCCAAGCTTTCAAGTGATACTGCG TGA-3').

Using the mixture of the two obtained PCR products as a template, another PCR was conducted with SEQ ID NO: 7 and SEQ ID NO: 10 to generate a fragment having an SfiI site between two ORFs, UL44h and UL45h.

The resulting fragment was then digested with EcoRI and HindIII and ligated to pUC18, which had been digested with EcoRI and HindIII. The obtained plasmid was designated p44/45Sfi.

For construction of double recombinant HVT in which two genes were inserted at UL44/45 and UL45/46 respectively, the UL46 gene was deleted from p44/45Sfi. p45/46Sfi (U.S. Pat. No. 7,569,365) digested with EcoRI and SfiI was ligated with dSfiI-EcoRI linker, resulting in plasmid p44/45d46. p44/45Sfi cleaved with SphI and PstI was ligated with p44/45d46 cleaved with the same enzymes, resulting in the plasmid p44/45d46Sfi.

Construction of pHVT 87-88

HVT DNA was prepared from CEF cells infected with the HVT FC126 strain according to the method of Lee et al. (J. Gen. Virol., 51:245-253, 1980). Using the obtained HVT DNA as a template, PCR was performed with two pairs of primers. Each primer was designed on the information of Genbank X68653.1. A DNA fragment having an SfiI site between two ORFs, US2 (HVT088) and SORF3 (HVT087), was prepared by PCR and cloned into pUC18.

The first pair was SEQ ID NO: 11 (5'-GGGAAT-TCGAAGAGCCCCCGCGGACG CATG-3') and SEQ ID NO: 12 (5'-CCGCTAGCGGCCGCAAGTTCCTTCAC-CATGA CCAG-3').

The second pair was SEQ ID NO: 13 (5'-GCGGCCGCTAGCGGCCTTATTGG CCGTAGCATAAA-GACGCAGG-3') and SEQ ID NO: 14 (5'-CCAAGCTTCTAGTACA TATATATACATGAC-3').

The first resulting fragment was digested with EcoRI and NheI. The second resulting fragment was digested with NheI and HindIII. These cleaved fragments were integrated into pUC18 cleaved with EcoRI and HindIII, resulting in the plasmid pHVT 87-88.

Construction of pHVT 86-87

HVT DNA was prepared from CEF cells infected with the HVT FC126 strain according to the method of Lee et al. (J. Gen. Virol., 51:245-253, 1980). Using the obtained HVT DNA as a template, PCR was performed with two pairs of primers. Each primer was designed on the information of Genbank X68653.1. A DNA fragment having an SfiI site between two ORFs, US10 (HVT086) and SORF3 (HVT087), was prepared by PCR and cloned into pUC18.

The first pair was SEQ ID NO: 15 (5'-GGGGGAATT-CATTATCCCATCTAACAGTTATATACG-3') and SEQ ID NO: 16 (5'-GCCGCTAGCGGCCGCCTTTAT-TAACAACCTTAC-3').

The second pair was SEQ ID NO: 17 (5'-GCGGCCGCTAGCGGCCTTATTGGCC GTTTATTC-TATGTAAGAC-3') and SEQ ID NO: 18 (5'-CCCAAGCT-TAAGTTCCTTC ACCATG-3').

The first resulting fragment was digested with EcoRI and NheI. The second resulting fragment was digested with NheI and HindIII. These cleaved fragments were integrated into pUC18 cleaved with EcoRI and HindIII, resulting in the plasmid pHVT 86-87.

Construction of the Homology Vector

Chemical Synthesized mCMV IE1 Promoter mCMV IE1 promoter (SEQ ID NO: 19) was synthesized on the information of 4191-4731 bp in Gene Bank L06816.1 reported by Koszinowski, U. H. Synthesized mCMV IE1 promoter was designed such that BglI-PstI sites were added in front of it and XbaI-NotI sites were added at the end.

```
SEQ ID NO: 19: GGCCAATAAG GCTGCAGTAC TGAGTCATTA

GGGACTTTCC AATGGGTTTT GCCCAGTACA TAAGGTCAAT

AGGGGTGAAT CAACAGGAAA GTCCCATTGG AGCCAAGTAC

ACTGAGTCAA TAGGGACTTT CCATTGGGTT TTGCCCAGTA

CAAAAGGTCA ATAGGGGGTG AGTCAATGGG TTTTTCCCAT

TATTGGCACG TACATAAGGT CAATAGGGGT GAGTCATTGG

GTTTTTCCAG CCAATTTAAT TAAAACGCCA TGTACTTTCC

CACCATTGAC GTCAATGGGC TATTGAAACT AATGCAACGT

GACCTTTAAA CGGTACTTTC CCATAGCTGA TTAATGGGAA

AGTACCGTTC TCGAGCCAAT ACACGTCAAT GGGAAGTGAA

AGGGCAGCCA AAACGTAACA CCGCCCCGGT TTTCCCCTGG

AAATTCCATA TTGGCACGCA TTCTATTGGC TGAGCTGCGT
```

-continued

TCTACGTGGG TATAAGAGGC GCGACCAGCG TCGGTACCGT

CGCAGTCTTC GGTCTGACCA CCGTAGAACG CAGAGCTCCT

CGCTGCAGGC GGCCGCTCTA GA.

Construction of p44/45 mCMV IE1 VP2 SPA

SfiI-cleaved p44-45d46Sfi was dephosphorylated by using Alkaline Phosphatase *Shewanella* sp. S1B1 Recombinant (PAP) (Funakoshi #DE110). The fragment was ligated with BglI-cleaved p45/46BacVP2, resulting in the plasmid p44/45d46 BacVP2. The synthesized mCMV IE1 promoter (BglI/XbaI) was ligated with p44/45d46 BacVP2 cleaved with EcoRV and XbaI, and p44/45d46 Bac VP2 cleaved with EcoRV and BglI, resulting in p44/45d46 mCMV IE1 VP2. The synthetized short polyA signal (SPA: SEQ NO: ID 20 CTGCAGGCGGCCGCT CTAGAGTCGACAATAAAAGATCTTTATTTTCATTA- GATC TGTGTGTTGGTTTTTGTGTGGC- CAATAAGGCC) was integrated into p44/45d46 mCMV IE1 VP2 cleaved with SalI and SfiI, resulting in the homology plasmid p44/45d46 mCMV IE1 VP2 SPA.

Experiment 2: Purifying Recombinant HVT in CEF Transfected with Each Transfer Vector Viral DNA of the HVT wild type, FC126 strain (wt-HVT) was prepared as described by Morgan et al. (*Avian* Diseases, 34:345-351, 1990). Viral DNAs of FW029 (rHVT/45-46PecF) and FW023 (rHVT/45-46BacVP2) were prepared in the similar method. The first double rHVT pattern was that the CEF cells were transfected with the prepared wt-HVT DNA and p45/46sv40VP2 PecF (ex. FW137). The second pattern was that the CEF cells were transfected with the prepared FW029 DNA and p44/45 mCMV IE1 VP2 (ex. FW141). The third pattern was that the CEF cells were transfected with the prepared FW023 DNA and p44/45 mCMV IE1 F (ex. FW142). The fourth pattern was that the CEF cells were transfected with the prepared FW029 DNA and pHVT87-88Bac VP (ex. FW144). The fifth pattern was that the CEF cells were transfected with the prepared FW023 and pHVT87-88Pec F (ex. FW145). These resulting recombinant viruses were plaque purified by staining plaques with the anti-NDV-F antibody and anti-IBDV-VP2 antibody.

Briefly, $10^7$ primary CEF cells were suspended in 100 μl of MEF-1 (LonzaLNJVD-1004) and co-transfected with 1 μg of the homology vector, for example, p44/45 mCMV IE1 F and pHVT Bac VP2, and 2 μg of HVT DNA, for example, FC126, FW029 and FW023, by electroporation. Electroporation was performed on Nucleofector II. Transfected cells were diluted in 20 ml of Leibovitz's L-15 (Gibco BRL, Cat. #41300-39), McCoy's 5A Medium (Gibco BRL, Cat. #21500-061) (1:1) and 4% calf serum (solution LM(+) medium), spread at 100 ul per well in a 96-well plate.

Incubate at 37° C. in 5% $CO_2$ until the plaques became visible, the cells were detached from plates by trypsinization, diluted in freshly prepared secondary CEF cells, transferred equally to two 96-well plates and incubated for 3 days to visualize the plaques. One of two plates was then stained with anti-VP2 monoclonal antibody R63 (ATCC #: HB-9490) as the primary antibody. After detecting the well containing the stained recombinant plaques, cells from the corresponding well of the other plate were recovered, diluted in fresh secondary CEF cells and transferred equally to two 96-well plates to complete the first round of purification. The purification procedure was repeated until every obtained plaque was stained positively by monoclonal antibody R63. After that, the double rHVT candidate was stained by the anti-NDV-F antibody 3-1G/5 (Morrison, T. G., Proc. Natl. Acad. Sci. U.S.A. 84:1020-1024, 1987) or anti-F rabbit serum. Finally, expression of proteins of every plaque of the candidate rHVT was confirmed by dual IFA staining. CEF cells infected by each rHVT were fixed with cold acetone-methanol (2:1), washed with PBS, reacted with antibody mixture (1:1000 diluted anti-F rabbit serum #35 and anti-VP2 mouse Mab R63) at 37° C. for 60 minutes. After washing 3 times with PBS, the cells reacted with fluorescent antibody mixture (1:1000 diluted Alexa Fluor 488 anti-rabbit and Alexa Fluor 546 anti-mouse provided by Invitrogen) at 37° C. for 60 minutes. After washing 3 times with PBS, they were observed by fluorescence microscope at magnification by 400 times.

Protein VP2 expression was detected by anti-VP2 Mab (R63) and Alexa Fluor 546. Protein F expression was detected by anti-F #35 rabbit serum and Alexa Fluor 488. When all plaques expressed both and VP2, we concluded purification was completed. FIG. 3 shows some examples of dual IFA.

The purified recombinant HVT was designated rHVT/ND/IBD.

Table 1 below shows the expression of the VP2 and protein F obtained from the different rHVT/ND/IBD Strain FW023 (HVT/45-46 Bac VP2) corresponds to a monovalent recombinant herpes virus used as control for VP2 expression, and FW029 (HVT/45-46 PecF) corresponds to a monovalent recombinant herpes virus used as control for protein F expression.

TABLE 1

Expression of the inserted NDV-F and IBDV-VP2 genes by rHVT/ND/IBD (Detection of fluorescence)

| | Primary antibody | | |
|---|---|---|---|
| Virus | anti-F antiserum | anti-VP2 monoclonal antibody (R63) rabbit | PBS |
| FW137 | +w | +w | − |
| FW129 | + | + | − |
| FW130 | + | + | − |
| FW141 | + | + | − |
| FW142 | + | + | − |
| FW144 | + | + | − |
| FW145 | + | + | − |
| FW029 | + | − | − |
| FW023 | − | + | − |
| FC126 | − | − | − |
| None | − | − | − |

+: detected ,
+w; weakly detected,
−: not detected

Experiment 3: Co-Expression of Two Proteins in CEF Infected with Double Recombinant HVTs 2 ml containing $2\times10^5$ CEF cells was infected with recombinant HVTs, and incubated at 37° C. in 5% $CO_2$ for 3 days.

Then the culture was centrifuged at 300 g for 3 minutes, and the precipitated cells were resuspended in 100 ul. Laemmli buffer (100 ul) was added to the cell suspension. The resultant mixture was then boiled for 5 min and 5 ul of them was subjected to 10% SDS-polyacrylamide gel electrophoresis. The electrophoresed proteins were transferred from SDS-GEL to a PVDF membrane (Immobilon-P, Millipore), which was blocked in 1% w/v non-fat milk powder in PBS at room temperature for one hour.

For F detection (FIG. 4A), the treated membrane was then reacted with the anti-F rabbit antiserum #35 in 500-fold dilution at room temperature for one hour, washed three times with PBS, and incubated for one hour with the biotinylated anti-rabbit goat antiserum.

For VP2 detection (FIG. 4B), the treated membrane was then reacted with the anti-VP2 Mab R63 in 500-fold dilution at room temperature for one hour, washed three times with PBS, and incubated for one hour with the biotinylated anti-mouse goat antiserum.

After washing three times with PBS, the membrane was incubated for one hour with an avidin-alkaline phosphatase complex, washed three times with PBS and one time with TBS (Tris-buffered saline), and reacted with BCIP-NBT (a substrate of alkaline phosphatase). As shown in FIG. 4A, a protein band of 60 kilodaltons (kDa) was observed only in the lane with rHVT/ND/IBD infected cells, which was the expected size of the F protein (➡). There was no band in the lane of rHVT/44-45BacVP2 (FW123).

Figure 1:
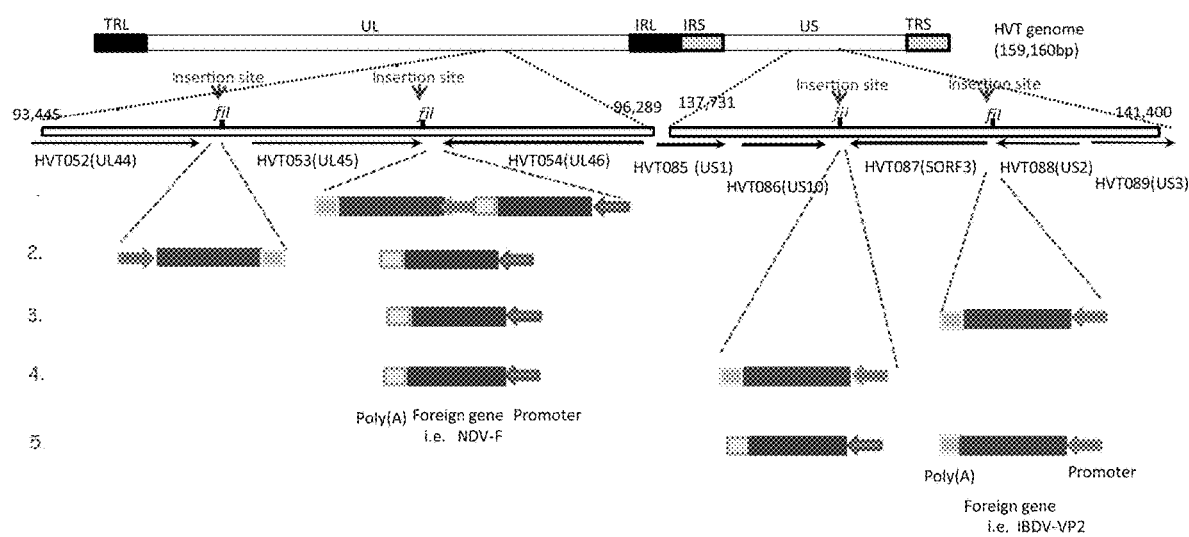
FIG. 1 illustrates the schematic diagram of the HVT genome. The location of the Unique Long (Ul) 44, UL45 and UL46 and the location of the Unique Short (US)10, SORF3 and US2 are marked. The recombinant nucleotide sequences can be inserted at PCR-generated SfiI sites between UL44 and UL45, and/or between UL45 and UL46, and/or between US10 and SORF3, and/or between SORF3 and US2.
Figure 2A:
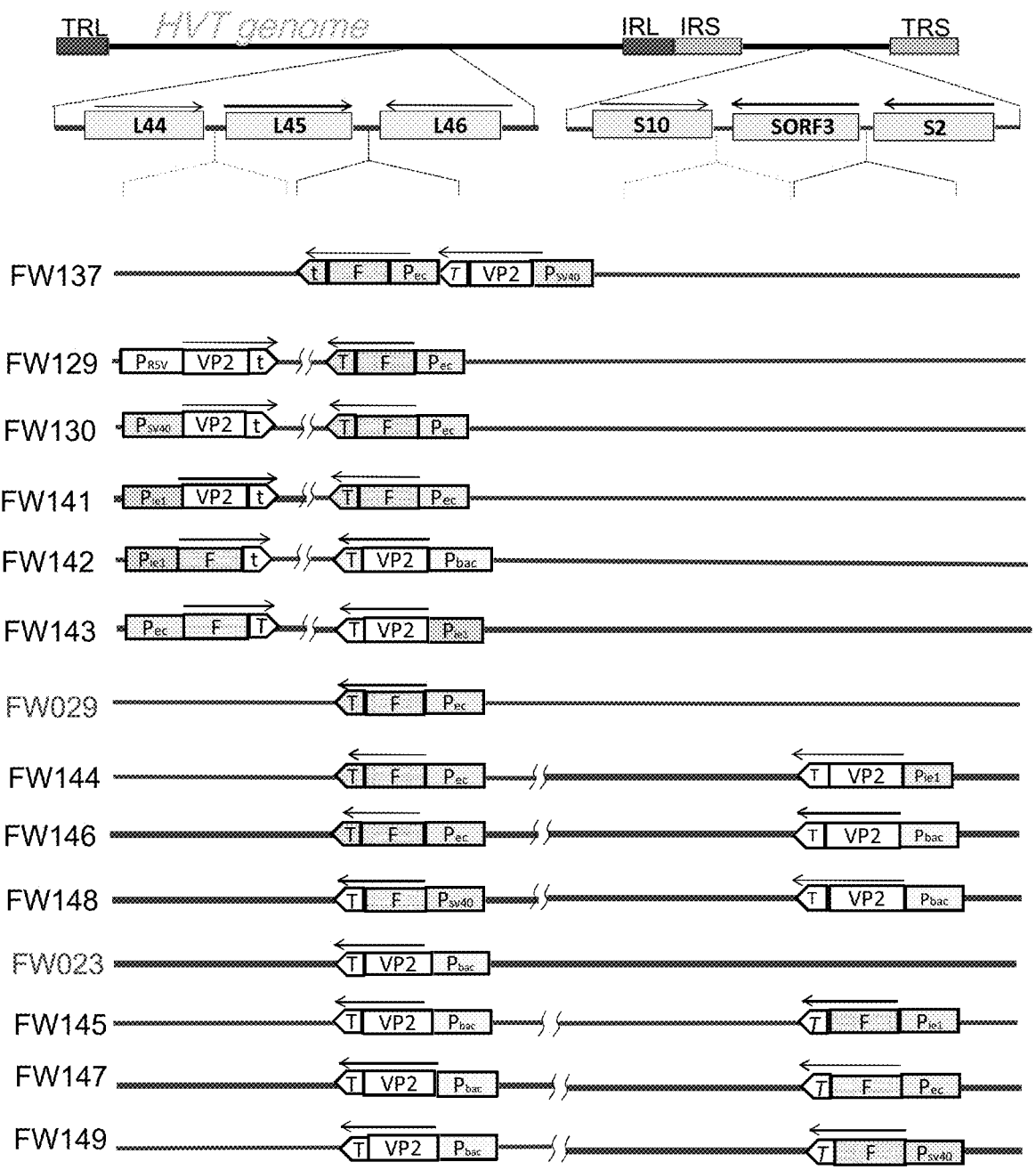
FIGS. 2A and 2B illustrate schematic diagrams of the HVT genome integrating different clusters of nucleotide sequences and promoters, according to particular embodiments of the invention.
Figure 2B:
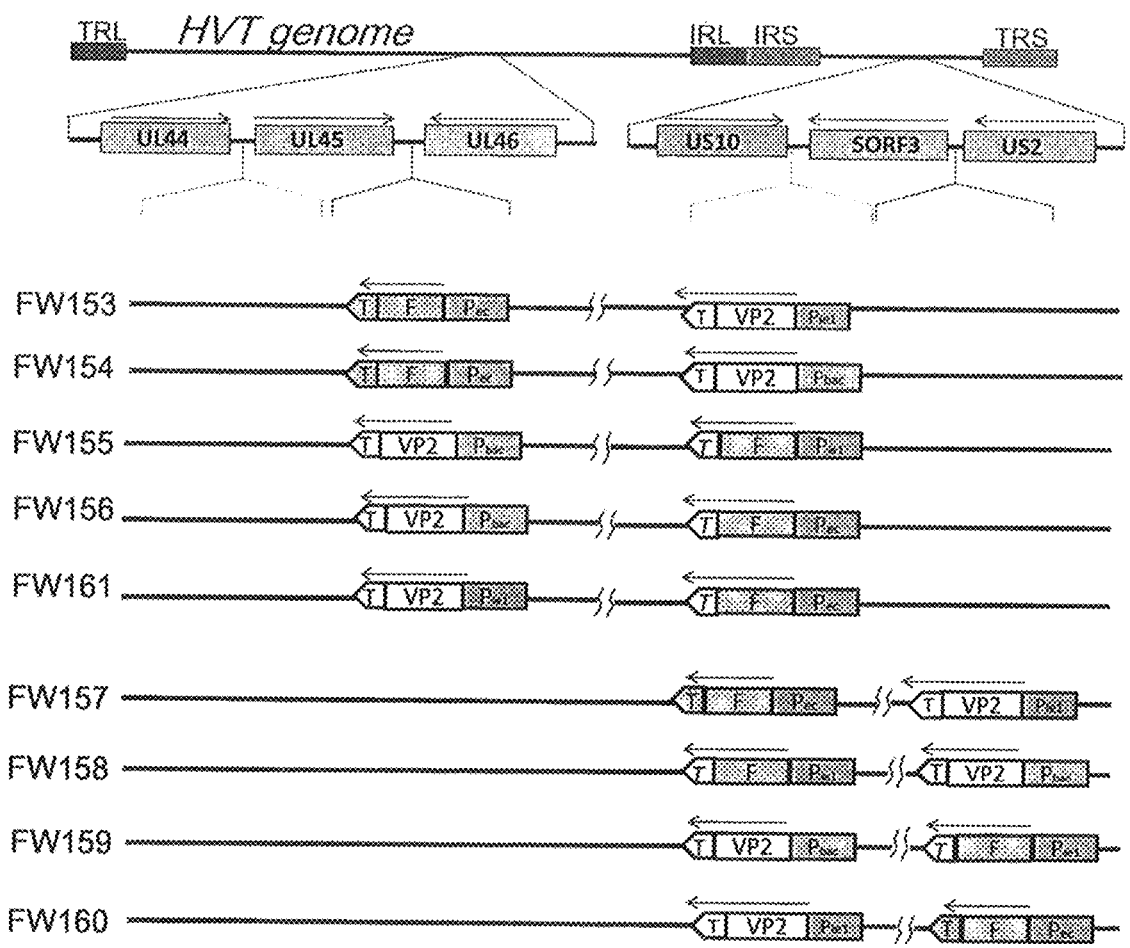

FIG. 3B shows VP2 protein was observed at 38 kilodaltons (kd) in the lanes of each rHVT/ND/IBD (⇨). On the contrary, there was no band in the lane of rHVT/PecF (FW029) (FIG. 1B). The 38 kd is the mature VP2 protein (A. A. Azad et al., 1987, Virol. 161:145-152; K. J., Fahey et al., 1985, J. Gen. Virol. 66:1479-1488).

Double recombinant HVTs according to the invention expressed both NDV-F and IBDV VP2.

Experiment 4: Verification of the Genomic Structure

Southern Blotting Analysis

The purified rHVT/ND/IBD was propagated on CEF cells of one 25-cm² flask to obtain the confluent plaques. Cells were recovered from dishes by scraping, transferred to Falcon tubes and subjected to centrifugation at 300×g for 5 min. Harvested cells were washed with PBS, resuspended in 0.6 ml of PBS and 0.4 ml of lysis buffer (1.25% TritonX-100, 250 mM 2-ME, and 50 mM EDTA in PBS), and lysed by vortexing for 3 min. The lysates were then centrifuged at 600×g for 5 min at room temperature and the supernatants were transferred to 15 ml Falcon tubes. The viruses were collected by centrifugation at 20,400×g for 20 min. The resultant pellets were then suspended in 0.33 ml of a nuclease solution (12.5 mM Tris-Cl (pH7.5), 1 µg/ml DNase I and 1 µg/ml RNase A), incubated at 37° C. for 30 min, and disrupted by incubating at 55° C. for 30 min with 83 µl of SDS-protease solution (50 mM EDTA, 5% SDS, 0.5 mg/ml protease K, and 28.5 mM 2-mercaptoethanol). The obtained mixture was treated twice with phenol-chloroform, and NaCl was added to the aqueous phase to the final concentration of 0.2 M. The viral DNA was precipitated by adding 2.5 volumes of ice-cold ethanol, washed with 70% ethanol and subjected to centrifugation at 20,400×g for 20 min at 4° C. After air-drying, the pellets were dissolved in TE buffer (10 mM Tris-Cl (pH8.0), 1 mM EDTA).

The viral DNA in TE buffer was digested with XhoI, SphI and SmaI, and subjected to 0.8% agarose gel electrophoresis. The electrophoresed DNA fragments on the single gel were transferred simultaneously to two nylon membranes (Molecular Cloning: A Laboratory Manual, third edition, 6.35, Sambrook, J., and Russell, D. W., Cold Spring Harbor Laboratory). After fixing DNA by baking, the immobilized DNA was hybridized with a DIG-labeled probe, "VP2 probe" or "IS44/45 probe", which was prepared with the PCR DIG Probe Synthesis Kit (Roche Diagnostics, Cat. #1636090). In addition, the viral DNA in TE buffer was digested with XhoI and SphI, and hybridized with a DIG-labeled probe, "F probe" or "IS45/46 probe", by the same procedure mentioned above. The VP2 probe was prepared with VP2 STC-F (SEQ ID NO: 21) and VP2 STC-R (SEQ ID NO: 22) as primers and p45/46bacVP2-STC as a template. The F probe was prepared with F-F (SEQ ID NO: 23) and F-R (SEQ ID NO: 24) as primers and p45/46PecF as a template. The IS45/46 probe was prepared with 45/46-F (SEQ ID NO: 25) and 45/46-R (SEQ ID NO: 26) as primers and pNZ45/46Sfi as a template. The IS44/45 probe was prepared with 44/45-F (SEQ ID NO: 27) and 44/45-R (SEQ ID NO: 28) as primers and pNZ44/45d46Sfi as a template.

```
VP2 STC-F
                                            (SEQ ID NO: 21)
5'-CACCGTCCTCAGCTTACCCACATC-3'

VP2 STC-R
                                            (SEQ ID NO: 22)
5'-ACGACGGATCCTGTTGCCACTCT-3'

NDV-F-F
                                            (SEQ ID NO: 23)
5'-CTAGCAGTGGCAGTTGGGAAGAT-3'

NDV-F-R
                                            (SEQ ID NO: 24)
5'-GTTAAGGCAGGGGAAGTGATTTGT-3'

45/46-F
                                            (SEQ ID NO: 25)
5'-GGGGAAGTCTTCCGGTTAAGGGAC-3'

45/46-R
                                            (SEQ ID NO: 26)
5'-GGTGCAATTCGTAAGACCGATGGG-3'

44/45-F
                                            (SEQ ID NO: 27)
5'-GTACTATAGAATGTGTTCC-3'

44/45-R
                                            (SEQ ID NO: 28)
5'-GTATCCAACGCCTCAAGATC-3'
```

The results of Southern blotting showed (FIGS. 5A-5D) that a 2077-bp fragment was hybridized to the VP2 probe in the DNA from FW129. In contrast, no band was detected in p45/46Pec F.

In addition a 2744-bp fragment was hybridized to the F probe in the DNA from each double recombinant HVT. No band was detected in the p45/46 SfiI.

2077-bp and 1228-bp fragments to IS44/45 probe in the DNA from FW129. 1350-bp fragment to IS44/45 probe in p45/46 PecF, which was inserted no gene at the IS44/45 site.

2744-bp and 770-bp fragments to IS45/46 probe in the DNA from each double recombinant HVT. FIG. 5A-5D indicated that the obtained double recombinants HVT/ND/IBD have the expected genomic structure.

Experiment 5: Stability of the Recombinant HVTs in Passage

Western Blotting Analysis

Double recombinant HVTs were passaged serially (up to 15 times) on chicken embryo fibroblasts (CEF). Then cell lysates were applied to Western blot analysis. In a first panel (FIG. 6A), the blot was reacted with an anti-F rabbit serum (#35). In a second panel (FIG. 6B) the blot was reacted with an anti-VP2 Mab (R63). Mock: non-infected CEF; M: Precision Plus Protein Standards Bio Rad #161-0374.

After 15 passages, F and VP2 were expressed stably in CEF infected with double recombinant HVT. However, FW137 expressed no signal of F and VP2 antigens after 15 passages, indicating that recombinant HVT which has two genes at a single site is unstable.

Southern Blotting Analysis
M: Molecular marker ramda HindIII digest
TP-24: transfer plasmid p44-45d46SV40VP2
TP-25: transfer plasmid p44-45d46RsvVP2

Each rHVT/ND/IBD was passaged fifteen times in CEF cells and subjected to Southern blot analysis as described in Experiment 4. The results were the same as those obtained in Experiment 4, indicating that the recombinant virus was stable even after 15 passages.

Figure 7A:
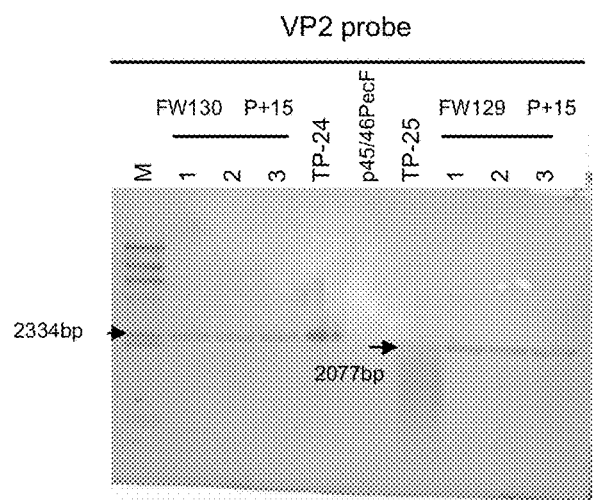

The results of Southern blotting show in FIG. 7A that a 2077-bp fragment was hybridized to the VP2 probe in the DNA from FW129. A 2334-bp fragment was hybridized to the VP2 probe in the DNA from FW130. In contrast, no band was detected in p45/46Pec F.

Figure 7B:
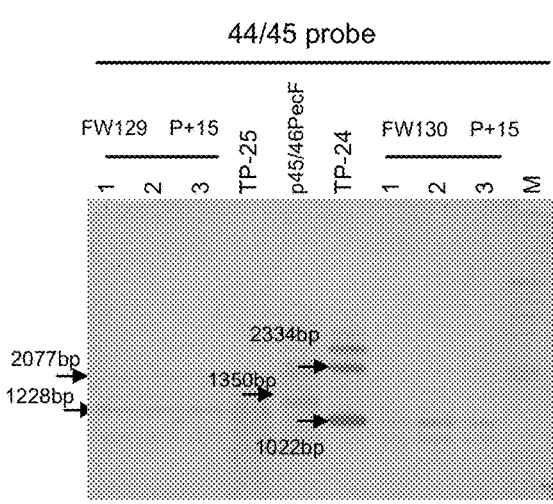
Figure 7C:
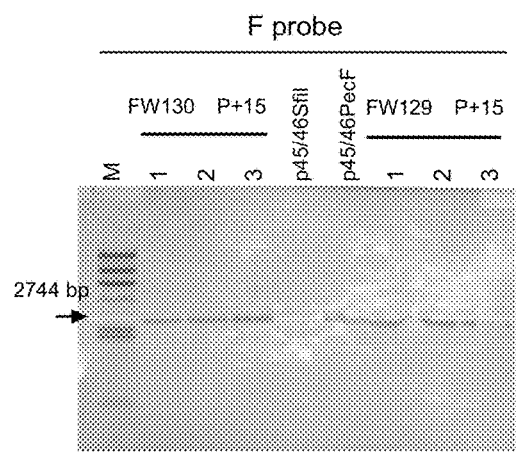

FIG. 7C shows that a 2744-bp fragment was hybridized to the F probe in the DNA from each double recombinant HVT. No band was detected in the p45/46 SfiI.

FIG. 7B shows that 2077-bp and 1228-bp fragments were hybridized to the IS44/45 probe in the DNA from FW129, and 2334-bp and 1022-bp fragments were hybridized to the IS44/45 probe in the DNA from FW130. A 1350-bp fragment was hybridized to the IS44/45 probe in p45/46 PecF, which contained no gene at the IS44/45 site.

Figure 7D:
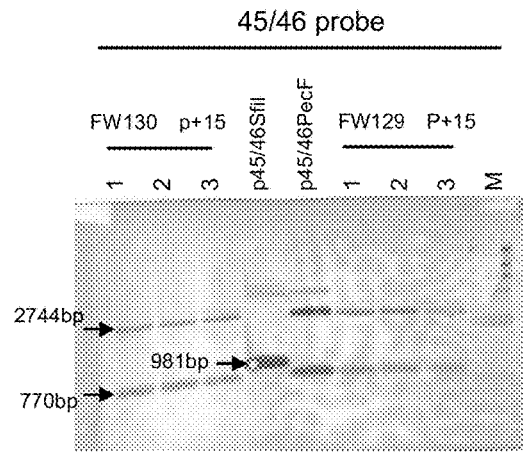

FIG. 7D shows that 2744-bp and 770-bp fragments were hybridized to the IS45/46 probe in the DNA from each double recombinant HVT.

Southern blotting with the 44/45 probe and 45/46 probe showed the VP2 gene or F gene stably maintained at the insertion site 44/45 or 45/46 respectively in FW129 and FW130.

Experiment 6: Anti-NDV and IBDV ELISA Titer in Chickens Inoculated with Double Recombinant HVTs 3,000 PFU/200 µl/bird of each rHVT/ND/IBD were inoculated subcutaneously into the backs of ten one-day-old SPF chickens (Line M, Japan Biological Laboratories) using a 20-gauge syringe. From three weeks post-vaccination onward, the serum was collected from the vaccinated birds. The anti-NDV antibody titer was measured by a commercial ELISA kit (IDEXX, ELISA kit to diagnose Newcastle Disease). The anti-IBDV antibody was titrated by a commercial ELISA kit, Flock Check infectious Bursal Disease Antibody Test Kit (IDEXX Laboratory, Inc.). Chickens of the negative control group (non-immunized) were not administered with any vaccine.

FIG. 8A shows change of anti-NDV titer. FIG. 8B shows change of anti-IBDV titer.

Double recombinant HVT using two sites stably induced both anti-NDV and anti-IBDV titers.

Experiment 7: Efficacy of rHVT/ND/IBD in SPF Chickens Against NDV

The efficacy of rHVT/ND/IBD (FW130, FW135, FW137, and FW129) as a Newcastle disease vaccine was evaluated using the efficacy test.

3,000 PFU/200 µl/bird of rHVT/ND were inoculated subcutaneously into the backs of ten one-day-old SPF chickens (Line M, Japan Biological Laboratories) using 20 Gauge syringe. From three weeks post-vaccination onward, the serum was collected from the vaccinated birds and the anti-NDV antibody titer was measured by a commercial ELISA kit (IDEXX, ELISA kit to diagnose Newcastle Disease).

Chickens of the positive control group were vaccinated at 14 days of age with a commercial NDV live vaccine according to the vendor's recommendation. Chickens of the negative control group were not administered with any vaccine.

At 43 days of age (42 days post-vaccination), chickens of all seven groups were challenged with $10^3 EID_{50}$ of NDV-TexasGB, the standard challenge strain in the United States, intramuscularly to the femoral region. The challenged chickens were observed daily to check mortality and to detect any symptoms of Newcastle disease.

TABLE 2

Challenge experiments of rHVT/ND/IBD-vaccinated SPF chickens with virulent NDV

| Vaccination | Dose (PFU/chicken) | No. of chickens | No. of symptom/total (%) | HI (ELISA) titer at hatch | ELISA titer at challenge |
|---|---|---|---|---|---|
| FW130 | 3000 | 10 | 0/10 (0) | 0 | 0.649 |
| FW135 | 3600 | 10 | 2/10(20) | | 0.085 |
| FW137 | 3600 | 10 | 3/10(30) | | 0.050 |
| FW129 | 3000 | 10 | 0/10(0) | | 0.233 |
| FW029 | 4000 | 10 | 0/10(0) | | 0.544 |
| Commercial NDV Live vaccine | On label | 10 | 0/10 (0) | | 1.089 |
| Challenge Controls | N/A | 10 | 11/12 (92) | | 0.089 |
| Non-challenge Controls | N/A | 10 | 0/5 (0) | | N/A |

As shown in Table 2, chickens vaccinated with rHVT/ND/IBD of the invention did not show any clinical signs and the ELISA titer at the day of challenge was significantly elevated. As expected, both chickens vaccinated with FW137 (wherein two recombinant nucleotide sequences are inserted into the same insertion site) or FW135 (wherein the Bac promoter is inserted between UL44 and UL45) show clinical signs, and the ELISA titer was weak.

Experiment 8: Efficacy of rHVT/ND/IBD in SPF Chickens Against IBDV

The efficacy of FWI29 and FW141 (HVT/45-46 PecF/44-45 mCMV IE1 VP2) as an IBD vaccine was evaluated by challenge IBDV STC.

First, 2,000 pfu of rHVT/ND/IBD were inoculated into SPF embryonating chicken eggs at day 18 or subcutaneously into the backs of one-day-old SPF chickens. At three weeks old, vaccinated chickens were challenged orally with $10^{3.5} EID_{50}$/bird of IBDV STC. One week later, all chickens were weighed and necropsied to recover the bursae of Fabricius, which were observed for any lesions caused by Infectious Bursal Disease.

The protection was evaluated by two criteria which are as follows. (1) The weight ratio of the bursa to the body (B/B index) was not statistically different from that of non-vaccinated, non-challenged chickens. (2) No malformation of the bursa of Fabricius such as edematization, hemorrhage, yellowish exudate, discoloration, atrophy, or gelatinous exudate was detected. The results were summarized in Table 3.

TABLE 3

Challenge experiments of rHVT/ND/IBD-vaccinated SPF chickens with virulent IBDV

| Vaccination | | # Protected/total |
|---|---|---|
| Vaccine | Route | (%) |
| FW129 | SQ | 7/8 (88%) |
| FW141 | SQ | 8/8 (100%) |
| FW023 | SQ | 8/8 (100%) |
| FW129 | In ovo | 8/10 (80%) |
| FW141 | In ovo | 9/10 (90%) |
| FW023 | In ovo | 9/10 (90%) |
| None | N/A | 0/4 (0%) |
| None | N/A | 5/5 (100%) |

More than 80% of all vaccinated chickens were protected against the challenge with IBDV STC strain, indicating that rHVT/ND/IBD can induce protective immunity in chickens against virulent IBDV.

Experiment 9: IBDV Challenge Trial at 8 Weeks in MDA+ Chickens

Groups
G1: NINC (not vaccinated, not challenged)
G2: NICC (not vaccinated, challenged)
G3: FW141
G4: FW144
G5: FW023 (positive control)
Chicks
MDA+ birds (layers), 16 to 17 birds in each group.

Three thousand pfu of vaccines were inoculated subcutaneously into the backs of 16 to 17 one-day-old MDA+ chickens. At 8 weeks old, vaccinated chickens were challenged orally with $10^3$ TCID$_{50}$/bird of IBDV STC. One week later, all chickens were weighed and necropsied to recover the bursae of Fabricius, which were observed for any lesions caused by Infectious Bursal disease.

The protection was evaluated by the two following criteria: (1) The weight ratio of the bursa to the body (B/B index); (2) No malformation of the bursa of Fabricius such as edematization, hemorrhage, yellowish exudate, discoloration, atrophy, or gelatinous exudate was detected. The results are summarized in the following table.

| | n | B/B Index | dead | lesion | of protection |
|---|---|---|---|---|---|
| NINC | 10 | 1.00 | 0 | 0/16 | — |
| NICC | 16 | 0.44 | 1 | 16/16 | 0 |
| FW141 | 16 | 0.94 | 0 | 2/16 | 88 |
| FW144 | 10 | 0.93 | 1 | 5/16 | 69 |
| FW023 | 17 | 0.98 | 0 | 3/17 | 82 |

These results show that the multivalent vaccine of the invention causes effective protection in vivo against IBDV.

Experiment 10: NDV Challenge Trial at 8 Weeks in MDA+ Chickens

Group
G1: challenge control
G2: FW141
G3: FW144
G4: FW145
G5: FW029 (positive control)
Chicks
MDA+ birds (layers), 17 birds in each group.

Three thousand PFU of vaccines were inoculated subcutaneously into the backs of 17 one-day-old MDA+ chickens. At 8 weeks old, vaccinated chickens were challenged with $10^3$ EID$_{50}$ of NDV-TexasGB, the standard challenge strain in the United States, intra-muscularly to the femoral region. The challenged chickens were observed daily to check mortality and to detect any symptoms of Newcastle disease. The results are presented below.

| | Immunized | Challenged | Dead | Symptom* | % protection |
|---|---|---|---|---|---|
| Challenge control | 17 | 13 | 13 | 0 | 0.0 |
| FW141 | 17 | 15 | 1 | 0 | 93.3 |
| FW144 | 17 | 15 | 3 | 1 | 73.3 |
| FW145 | 17 | 13 | 0 | 0 | 100.0 |
| FW029 | 17 | 16 | 3 | 0 | 81.3 |

*some NDV symptoms without death

These results show that the multivalent vaccine of the invention causes effective protection in vivo against NDV and IBDV. The protection is strong and stable.

We claim:

1. A recombinant herpes virus of turkeys (HVT), which comprises:
   (i) a recombinant nucleotide sequence encoding a glycoprotein B (gB) protein of infectious laryngotracheitis virus (ILTV) or an immunogenic fragment thereof, inserted into a non-coding region of the viral genome located between UL45 and UL46; and
   (ii) a recombinant nucleotide sequence encoding a F protein of Newcastle Disease Virus (NDV) or an immunogenic fragment thereof, inserted into a non-coding region of the viral genome located between US10 and SORF3,
   and wherein, upon infection of Chicken Embryo Fibroblasts (CEF) with said recombinant HVT, the recombinant nucleotide sequence encoding a gB protein and the recombinant nucleotide sequence encoding a F protein of NDV are co-expressed in said CEF cells after 10 passages.

2. The recombinant HVT of claim 1, wherein each recombinant nucleotide sequence is under control of a promoter selected from the chicken beta-actin (Bac) promoter, the Pec promoter, the Murine Cytomegalovirus (Mcmv) immediate-early (ie)1 promoter, the Human Cytomegalovirus promoter (Hcmv), the Simian virus (SV)40 promoter, and the Raus Sarcoma virus (RSV) promoter, or any fragments thereof which retain a promoter activity.

3. The recombinant HVT of claim 1, wherein the recombinant nucleotide sequence encoding a gB protein of ILTV or an immunogenic fragment thereof is under control of a Pec promoter.

4. The recombinant HVT of claim 1, which comprises:
   (i) a recombinant nucleotide sequence encoding a gB protein of ILTV or an immunogenic fragment thereof, under control of a Pec promoter, inserted into a non-coding region of the viral genome located between UL45 and UL46; and
   (ii) a recombinant nucleotide sequence encoding a F protein of Newcastle Disease Virus or an immunogenic fragment thereof, under control of a Pec promoter, inserted into a non-coding region of the viral genome located between US10 and SORF3.

5. A multivalent vaccine which comprises an effective immunizing amount of a recombinant HVT of claim 1.

6. A method for vaccinating an *avian*, comprising administering to said *avian* a multivalent vaccine of claim 5.

7. A vaccination kit for immunizing an *avian*, which comprises the following components:
   a) an effective amount of the vaccine of claim 5, and
   b) a means for administering said vaccine to said *avian*.

* * * * *

SEQUENCE LISTING

<160> NUMBER OF SEQ ID NOS: 28

<210> SEQ ID NO 1
<211> LENGTH: 1506
<212> TYPE: DNA
<213> ORGANISM: artificial
<220> FEATURE:
<223> OTHER INFORMATION: Bac promoter

<400> SEQUENCE: 1

```
tgcagctcag tgcatgcacg ctcattgccc atcgctatcc ctgcctctcc tgctggcgct    60
ccccgggagg tgacttcaag gggaccgcag gaccacctcg ggggtggggg gagggctgca   120
cacgcggacc ccgctccccc tcccaacaa agcactgtgg aatcaaaaag ggggagggg    180 ggatggaggg gcgcgtcaca cccccgcccc acaccctcac ctcgaggtga gcccacgtt   240
```

```
ctgcttcact ctccccatct ccccccccct cccaccccca attttgtatt tatttatttt    300
ttaattattt tgtgcagcga tgggggcggg ggggggggggg gcgcgcgcca ggcggggcgg    360
ggcggggcca ggggcggggc ggggcgaggc ggagaggtgc ggcggcagcc aatcagagcg    420
gcgcgctccg aaagtttcct tttatggcga ggcggcggcg gcggcggccc tataaaaagc    480
gaagcgcgcg gcgggcggga gtcgctgcgc gctgccttcg ccccgtgccc cgctccgccg    540
ccgcctcgcg ccgcccgccc cggctctgac tgaccgcgtt actcccacag gtgagcgggc    600
gggacggccc ttctcctccg ggctgtaatt agcgcttggt ttaatgacgg ctcgtttctt    660
ttctgtggct gcgtgaaagc cttaaagggc tccgggaggg ccctttgtgc ggggggggagc   720
ggctcggggg gtgcgtgcgt gtgtgtgtgc gtggggagcc ccgcgtgcgg ctccgcgctg    780
cccggcggct gtgagcgctg cgggcgcggc gcgggctttt gtgcgctccg cagtgtgcgc    840
gaggggagcg cggccggggg cggtgccccg cggtgcgggg ggggctgcga ggggaacaaa    900
ggctgcgtgc ggggtgtgtg cgtggggggg tgagcagggg gtgtgggcgc ggcggtcggg    960
ctgtaacccc ccctgcacc ccctccccg aagttgctga gcacggcccg gcttcgggtg     1020
cggggctccg tgcggggcgt ggcgcggggc tcgccgtgcc gggcgggggg tggcggcagg    1080
tggggtgcc gggcggggcg gggccgcctc gggccggga gggctcgggg gaggggcgcg     1140
gcggcccccg gagcgccggc ggctgtcgag gcgcggcgag ccgcagccat tgccttttat    1200
ggtaatcgtg cgagagggcg cagggacttc ctttgtccca aatctgtgcg gagccgaaat    1260
ctgggaggcg ccgccgcacc ccctctagcg ggcgcgggc gaagcggtgc ggcgccggca    1320
ggaaggaaat gggcggggag ggccttcgtg cgtcgccgcg ccgccgtccc cttctccatc    1380
tccagcctcg gggctgtccg caggggggacg gctgccttcg ggggggacgg ggcagggcgg   1440
ggttcggctt ctggcgtgtg accggcgggg tttatatctt cccttctctg ttcctccgca    1500
gccccc                                                              1506

<210> SEQ ID NO 2
<211> LENGTH: 557
<212> TYPE: DNA
<213> ORGANISM: artificial
<220> FEATURE:
<223> OTHER INFORMATION: Pec promoter

<400> SEQUENCE: 2
tgcagagtta ttaatagtaa tcaattacgg ggtcattagt tcatagccca tatatggagy    60
tccgcgttac ataacttacg gtaaatggcc cgcccggctga ccgcccaacg accccccgccc   120
attgacgtca ataatgacgt atgytcccat agtaacgcca tagggactt tccattgacg    180
tcaatgggtg gagtayttac ggtaaactgc ccattggcag tacatcaagt gtatcatatg    240
ccaagtacgc cccctattga cgtcaatgac ggtaaatgga tgcagtattt tgtgcagcga    300
tggggggcggg ggggggggggc gcgcgccagg cggggcgggg cggggcgagg ggcggggcgg   360
ggcgaggcgg agaggtgcgg cggcagccaa tcagagcggc gcgctccgaa agtttccttt    420
tatggcgagg cggcggcggc ggcggcccta taaaaagcga agcgcgcggc gggcgggagt    480
cgctgcgcgc tgccttcgcc ccgtgccccg ctccgccgcc gcctcgcgcc gcccgccccg    540
gctctgactg accgcgt                                                   557

<210> SEQ ID NO 3
<211> LENGTH: 541
<212> TYPE: DNA
<213> ORGANISM: artificial
```

```
<220> FEATURE:
<223> OTHER INFORMATION: Mcmv ie1 promoter

<400> SEQUENCE: 3
tactgagtca ttagggactt tccaatgggt tttgcccagt acataaggtc aatagggtg      60 aatcaacagg aaagtcccat tggagccaag tacactgagt caatagggac tttccattgg    120
gttttgccca gtacaaaagg tcaatagggg gtgagtcaat gggttttcc cattattggc     180 acgtacataa ggtcaatagg ggtgagtcat tgggttttc cagccaattt aattaaaacg     240
ccatgtactt tcccaccatt gacgtcaatg gctattgaa actaatgcaa cgtgaccttt     300
aaacggtact ttcccatagc tgattaatgg gaaagtaccg ttctcgagcc aatacacgtc    360
aatgggaagt gaaagggcag ccaaaacgta acaccgcccc ggttttcccc tggaaattcc    420
atattggcac gcattctatt ggctgagctg cgttctacgt gggtataaga ggcgcgacca    480
gcgtcggtac cgtcgcagtc ttcggtctga ccaccgtaga acgcagagct cctcgctgca    540
g                                                                    541

<210> SEQ ID NO 4
<211> LENGTH: 589
<212> TYPE: DNA
<213> ORGANISM: artificial
<220> FEATURE:
<223> OTHER INFORMATION: Hcmv promoter

<400> SEQUENCE: 4
gagttattaa tagtaatcaa ttacggggtc attagttcat agcccatata tggagttccg     60
cgttacataa cttacggtaa atggcccgcc ggctgaccgc ccaacgaccc ccgcccattg    120
acgtcaataa tgacgtatgt tcccatagta acgccaatag ggactttcca ttgacgtcaa    180
tgggtggagt atttacggta aactgcccat tggcagtaca tcaagtgtat catatgccaa    240
gtacgccccc tattgacgtc aatgacggta aatggcgcgc ctggcattat gcccagtaca    300
tgaccttatg ggactttcct acttggcagt acatctacgt attagtcatc gctattacca    360
tggtgatgcg gttttggcag tacatcaatg ggcgtggata gcggtttgac tcacggggat    420
ttccaagtct ccaccccatt gacgtcaatg ggagtttgtt ttggcaccaa aatcaacggg    480
actttccaaa atgtcgtaac aactccgccc cattgacgca aatgggcggt aggcgtgtac    540
ggtgggaggt ctatataagc agagctggtt tagtgaaccg tcagatcct                589

<210> SEQ ID NO 5
<211> LENGTH: 646
<212> TYPE: DNA
<213> ORGANISM: artificial
<220> FEATURE:
<223> OTHER INFORMATION: SV40 promoter

<400> SEQUENCE: 5
gcgcagcacc atggcctgaa ataacctctg aaagaggaac ttggttaggt accttctgag     60
gcggaaagaa ccagctgtgg aatgtgtgtc agttagggtg tggaaagtcc ccaggctccc    120
cagcaggcag aagtatgcaa agcatgcatc tcaattagtc agcaaccagg tgtggaaagt    180
ccccaggctc cccagcaggc agaagtatgc aaagcatgca tctcaattag tcagcaacca    240
tagtcccgcc cctaactccg cccatcccgc cctaactccg cccagttccg cccattctc     300 cgccccatgg ctgactaatt tttttttattt atgcagaggc cgaccgcctc ggcctctgag    360
ctattccaga agtagtgagg aggcttttttt ggaggcctag gcttttgcaa aaagcttgat    420
```

```
tcttctgaca caacagtctc gaacttaagc cgcagaagtt ggtcgtgagg cactgggcag    480
gtaagtatca aggttacaag acaggtttaa ggagaccaat agaaactggg cttgtcgaga    540
cagagaagac tcttgcgttt ctgataggca cctattggtc ttactgacat ccactttgcc    600
tttctctcca caggtgtcca ctccagttca attacagctc ttaagg                  646
```

<210> SEQ ID NO 6
<211> LENGTH: 534
<212> TYPE: DNA
<213> ORGANISM: artificial
<220> FEATURE:
<223> OTHER INFORMATION: RSV promoter

<400> SEQUENCE: 6

```
tgcatctgct ccctgcttgt gtgttggagg tcgctgagta gtgcgcgagc aaaatttaag     60
ctacaacaag gcaaggcttg accgacaatt gcatgaagaa tctgcttagg gttaggcgtt    120
ttgcgctgct tcgcgatgta cgggccagat atacgcgtat ctgagggggac tagggtgtgt    180 ttaggcgaaa agcggggctt cggttgtacg cggttaggag tccctcagg atatagtagt    240 ttcgcttttg catagggagg gggaaatgta gtcttatgca atactcttgt agtcttgcaa    300
catggtaacg atgagttagc aacatgcctt acaaggagag aaaaagcacc gtgcatgccg    360
attggtggaa gtaaggtggt acgatcgtgc cttattagga aggcaacaga cgggtctgac    420
atggattgga cgaaccactg aataccgcat tgcagagata attgtattta agtgcctagc    480
tcgatacaat aaacgccatt tgaccattca ccacattggt gtgcacctgg ctag          534
```

<210> SEQ ID NO 7
<211> LENGTH: 25
<212> TYPE: DNA
<213> ORGANISM: artificial
<220> FEATURE:
<223> OTHER INFORMATION: primer

<400> SEQUENCE: 7

```
ccccgaattc atggaagaaa tttcc                                           25
```

<210> SEQ ID NO 8
<211> LENGTH: 35
<212> TYPE: DNA
<213> ORGANISM: artificial
<220> FEATURE:
<223> OTHER INFORMATION: primer

<400> SEQUENCE: 8

```
cgcgggccaa taaggccaac atcgggacgt acatc                                35
```

<210> SEQ ID NO 9
<211> LENGTH: 36
<212> TYPE: DNA
<213> ORGANISM: artificial
<220> FEATURE:
<223> OTHER INFORMATION: primer

<400> SEQUENCE: 9

```
gcgcggcctt attggcctta aataccgcgt ttggag                               36
```

<210> SEQ ID NO 10
<211> LENGTH: 28
<212> TYPE: DNA
<213> ORGANISM: artificial
<220> FEATURE:
<223> OTHER INFORMATION: primer

<400> SEQUENCE: 10
ccccaagctt tcaagtgata ctgcgtga                                           28

<210> SEQ ID NO 11
<211> LENGTH: 30
<212> TYPE: DNA
<213> ORGANISM: artificial
<220> FEATURE:
<223> OTHER INFORMATION: primer

<400> SEQUENCE: 11
gggaattcga agagcccccg cggacgcatg                                         30

<210> SEQ ID NO 12
<211> LENGTH: 35
<212> TYPE: DNA
<213> ORGANISM: artificial
<220> FEATURE:
<223> OTHER INFORMATION: primer

<400> SEQUENCE: 12
ccgctagcgg ccgcaagttc cttcaccatg accag                                   35

<210> SEQ ID NO 13
<211> LENGTH: 43
<212> TYPE: DNA
<213> ORGANISM: artificial
<220> FEATURE:
<223> OTHER INFORMATION: primer

<400> SEQUENCE: 13
gcggccgcta gcggccttat tggccgtagc ataaagacgc agg                          43

<210> SEQ ID NO 14
<211> LENGTH: 30
<212> TYPE: DNA
<213> ORGANISM: artificial
<220> FEATURE:
<223> OTHER INFORMATION: primer

<400> SEQUENCE: 14
ccaagcttct agtacatata tatacatgac                                         30

<210> SEQ ID NO 15
<211> LENGTH: 36
<212> TYPE: DNA
<213> ORGANISM: artificial
<220> FEATURE:
<223> OTHER INFORMATION: primer

<400> SEQUENCE: 15
gggggaattc attatcccat ctaacagtta tatacg                                  36

<210> SEQ ID NO 16
<211> LENGTH: 33
<212> TYPE: DNA
<213> ORGANISM: artificial
<220> FEATURE:
<223> OTHER INFORMATION: primer

<400> SEQUENCE: 16
gccgctagcg gccgccttta ttaacaacct tac                                     33

<210> SEQ ID NO 17

```
<211> LENGTH: 43
<212> TYPE: DNA
<213> ORGANISM: artificial
<220> FEATURE:
<223> OTHER INFORMATION: primer

<400> SEQUENCE: 17
gcggccgcta gcggccttat tggccgttta ttctatgtaa gac        43

<210> SEQ ID NO 18
<211> LENGTH: 25
<212> TYPE: DNA
<213> ORGANISM: artificial
<220> FEATURE:
<223> OTHER INFORMATION: primer

<400> SEQUENCE: 18
cccaagctta agttccttca ccatg                            25

<210> SEQ ID NO 19
<211> LENGTH: 572
<212> TYPE: DNA
<213> ORGANISM: artificial
<220> FEATURE:
<223> OTHER INFORMATION: Mcmv ie1 promoter

<400> SEQUENCE: 19
ggccaataag gctgcagtac tgagtcatta gggactttcc aatgggtttt gcccagtaca   60
taaggtcaat aggggtgaat caacaggaaa gtcccattgg agccaagtac actgagtcaa  120
tagggacttt ccattgggtt tgcccagta  caaaaggtca ataggggtg  agtcaatggg  180 ttttccccat tattggcacg tacataaggt caataggggt gagtcattgg gttttccag   240 ccaatttaat taaaacgcca tgtactttcc caccattgac gtcaatgggc tattgaaact   300
aatgcaacgt gacctttaaa cggtactttc ccatagctga ttaatgggaa agtaccgttc   360
tcgagccaat acacgtcaat gggaagtgaa agggcagcca aaacgtaaca ccgcccggt    420 tttcccctgg aaattccata ttggcacgca ttctattggc tgagctgcgt tctacgtggg   480
tataagaggc gcgaccagcg tcggtaccgt cgcagtcttc ggtctgacca ccgtagaacg   540
cagagctcct cgctgcaggc ggccgctcta ga                                572

<210> SEQ ID NO 20
<211> LENGTH: 87
<212> TYPE: DNA
<213> ORGANISM: artificial
<220> FEATURE:
<223> OTHER INFORMATION: SPA; synthesized short polyA signal

<400> SEQUENCE: 20
ctgcaggcgg ccgctctaga gtcgacaata aaagatcttt attttcatta gatctgtgtg   60
ttggtttttt gtgtggccaa taaggcc                                      87

<210> SEQ ID NO 21
<211> LENGTH: 24
<212> TYPE: DNA
<213> ORGANISM: artificial
<220> FEATURE:
<223> OTHER INFORMATION: VP2 STC-F; primer

<400> SEQUENCE: 21
caccgtcctc agcttaccca catc                             24
```

```
<210> SEQ ID NO 22
<211> LENGTH: 23
<212> TYPE: DNA
<213> ORGANISM: artificial
<220> FEATURE:
<223> OTHER INFORMATION: VP2 STC-R; primer

<400> SEQUENCE: 22
acgacggatc ctgttgccac tct                                           23

<210> SEQ ID NO 23
<211> LENGTH: 23
<212> TYPE: DNA
<213> ORGANISM: artificial
<220> FEATURE:
<223> OTHER INFORMATION: NDV-F-F; primer

<400> SEQUENCE: 23
ctagcagtgg cagttgggaa gat                                           23

<210> SEQ ID NO 24
<211> LENGTH: 24
<212> TYPE: DNA
<213> ORGANISM: artificial
<220> FEATURE:
<223> OTHER INFORMATION: NDV-F-R; primer

<400> SEQUENCE: 24
gttaaggcag gggaagtgat ttgt                                          24

<210> SEQ ID NO 25
<211> LENGTH: 24
<212> TYPE: DNA
<213> ORGANISM: artificial
<220> FEATURE:
<223> OTHER INFORMATION: 45/46-F; primer

<400> SEQUENCE: 25
ggggaagtct tccggttaag ggac                                          24

<210> SEQ ID NO 26
<211> LENGTH: 24
<212> TYPE: DNA
<213> ORGANISM: artificial
<220> FEATURE:
<223> OTHER INFORMATION: 45/46-R; primer

<400> SEQUENCE: 26
ggtgcaattc gtaagaccga tggg                                          24

<210> SEQ ID NO 27
<211> LENGTH: 19
<212> TYPE: DNA
<213> ORGANISM: artificial
<220> FEATURE:
<223> OTHER INFORMATION: 44/45-F; primer

<400> SEQUENCE: 27
gtactataga atgtgttcc                                                19

<210> SEQ ID NO 28
<211> LENGTH: 20
<212> TYPE: DNA
<213> ORGANISM: artificial
<220> FEATURE:
<223> OTHER INFORMATION: 44/45-R; primer
```

```
<400> SEQUENCE: 28
gtatccaacg cctcaagatc                                                     20
```

UNITED STATES PATENT AND TRADEMARK OFFICE
CERTIFICATE OF CORRECTION

PATENT NO. : 11,730,807 B2  
APPLICATION NO. : 17/475385  
DATED : August 22, 2023  
INVENTOR(S) : Ayumi Fujisawa et al.

Page 1 of 1

It is certified that error appears in the above-identified patent and that said Letters Patent is hereby corrected as shown below:

In the Specification

Column 11,
Line 66, "UL5" should read --UL45--.

Signed and Sealed this
Twenty-sixth Day of December, 2023

Katherine Kelly Vidal
*Director of the United States Patent and Trademark Office*